(12) United States Patent
Harris

(10) Patent No.: US 11,793,404 B1
(45) Date of Patent: *Oct. 24, 2023

(54) HANDHELD TESTING DEVICE INCLUDING MULTIPLE TIMERS

(71) Applicant: ToxOptix, LLC, Montgomery, TX (US)

(72) Inventor: Royger Harris, Hutto, TX (US)

(73) Assignee: ToxOptix, LLC., Austin, TX (US)

( * ) Notice: Subject to any disclaimer, the term of this patent is extended or adjusted under 35 U.S.C. 154(b) by 97 days.

This patent is subject to a terminal disclaimer.

(21) Appl. No.: 16/945,332

(22) Filed: Jul. 31, 2020

Related U.S. Application Data

(60) Continuation of application No. 16/564,989, filed on Sep. 9, 2019, now abandoned, which is a continuation of application No. 15/642,623, filed on Jul. 6, 2017, now Pat. No. 10,405,743, which is a division of application No. 14/725,475, filed on May 29, 2015, now Pat. No. 9,700,203.

(60) Provisional application No. 62/051,380, filed on Sep. 17, 2014.

(51) Int. Cl.
*A61B 3/14* (2006.01)
*A61B 3/10* (2006.01)
*A61B 3/00* (2006.01)
*A61B 3/113* (2006.01)

(52) U.S. Cl.
CPC ............ *A61B 3/113* (2013.01); *A61B 3/0025* (2013.01); *A61B 3/0033* (2013.01); *A61B 3/0091* (2013.01); *A61B 3/145* (2013.01)

(58) Field of Classification Search
CPC ......... A61B 3/113; A61B 3/032; A61B 3/103; A61B 3/14; A61B 3/1208; A61B 3/1225; A61B 3/024; A61B 3/1015

USPC ............... 351/209–210, 200, 205–208, 218, 351/221–223, 246

See application file for complete search history.

(56) References Cited

U.S. PATENT DOCUMENTS

| | | |
|---|---|---|
| 7,309,125 B2 | 12/2007 | Pugach et al. |
| 7,338,166 B2 | 3/2008 | Waldorf et al. |
| 7,519,864 B2 | 4/2009 | Alam et al. |
| 7,819,527 B2 | 10/2010 | Bardenstein et al. |
| 8,064,886 B2 | 11/2011 | Hawkins et al. |
| 8,226,574 B2 | 7/2012 | Whillock et al. |
| 8,317,328 B1 | 11/2012 | Harris et al. |
| 8,764,194 B2 | 7/2014 | Harris |

(Continued)

*Primary Examiner* — Dawayne Pinkney
(74) *Attorney, Agent, or Firm* — Michael Best & Friedrich LLP

(57) ABSTRACT

A handheld evaluation device includes an image recorder configured to capture at least one of still images or video images, a function switch configured to operate the image recorder, a plurality of timers, each of which is associated with one or more portions of a substance evaluation protocol, and processing circuitry coupled to the image recorder, the function switch, and a plurality of actuators operatively associated with the plurality of timers. The processing circuitry is configured to initiate a first timer of the plurality of timers in response to detecting the activation of a first actuator of the plurality of actuators, activate the image recorder in response to detecting operation of the function switch, provide feedback associated with the first timer, determine completion of the first timer, and store in memory the at least one of still images or video images captured by the image recorder.

20 Claims, 13 Drawing Sheets

(56) References Cited

U.S. PATENT DOCUMENTS

| | | | |
|---|---|---|---|
| 8,783,870 B2 | 7/2014 | Harris et al. | |
| 8,899,748 B1 | 12/2014 | Migdal | |
| 9,380,958 B2 | 7/2016 | Harris | |
| 2003/0137588 A1* | 7/2003 | Wang | H04N 5/2252 |
| | | | 348/E5.026 |
| 2004/0056949 A1* | 3/2004 | Lin | B43K 29/00 |
| | | | 348/207.99 |
| 2010/0280372 A1 | 11/2010 | Poolman et al. | |
| 2013/0057829 A1* | 3/2013 | Harris | A61B 5/4845 |
| | | | 351/209 |
| 2014/0002797 A1 | 1/2014 | Harris | |
| 2014/0210627 A1 | 7/2014 | Nothacker et al. | |
| 2015/0015692 A1 | 1/2015 | Smart | |
| 2015/0077712 A1 | 3/2015 | Geersten | |
| 2016/0023631 A1 | 1/2016 | Chu | |

* cited by examiner

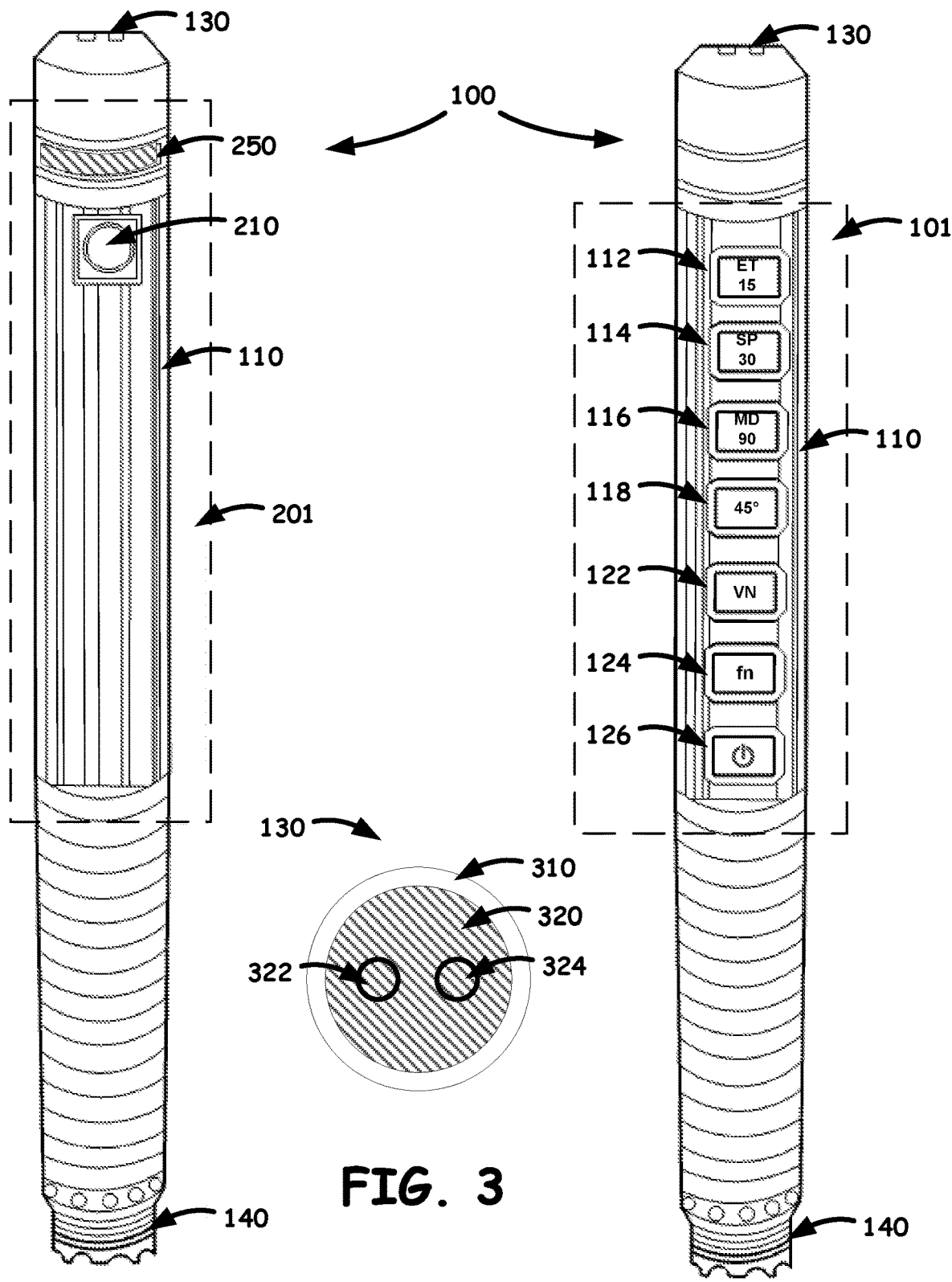

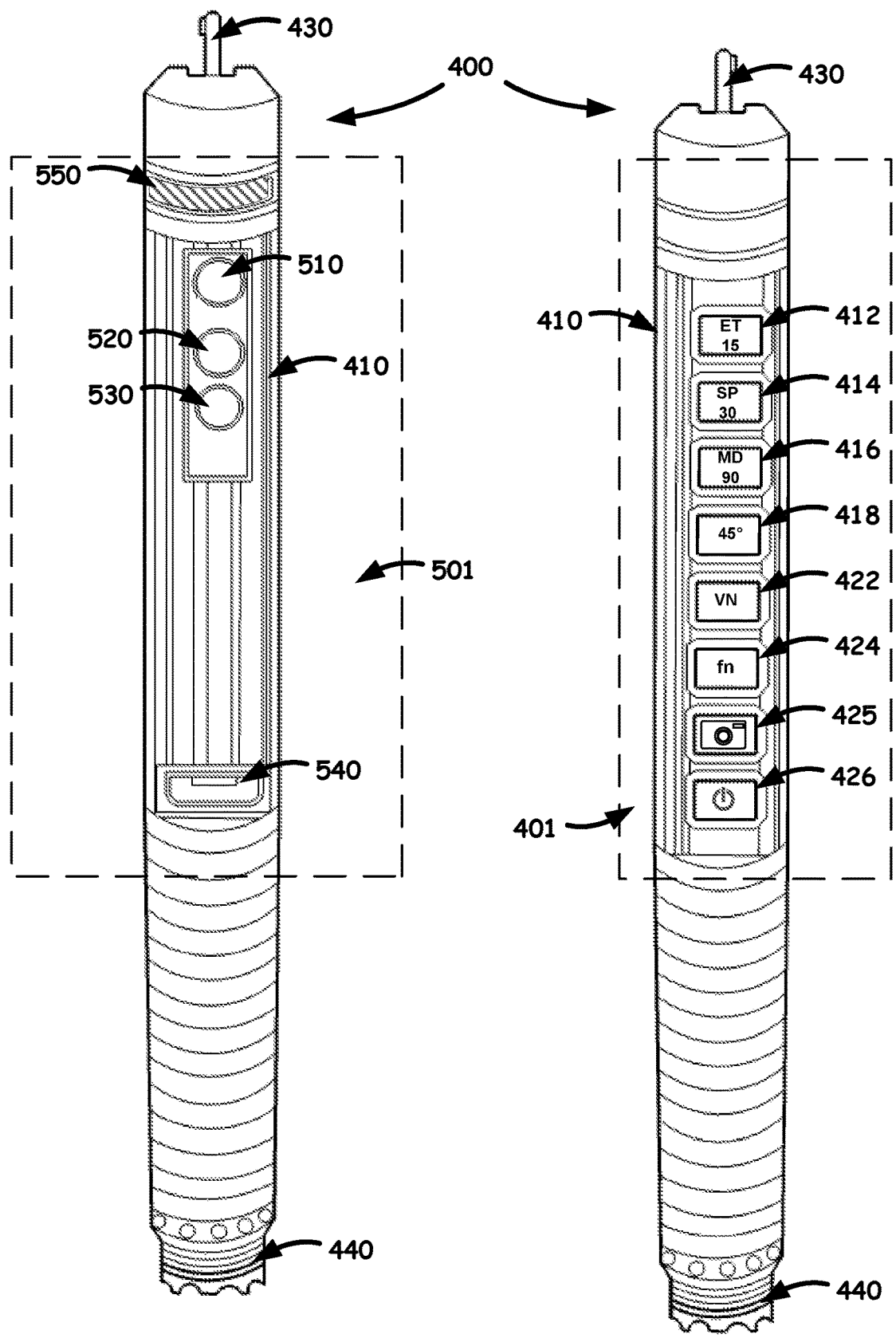

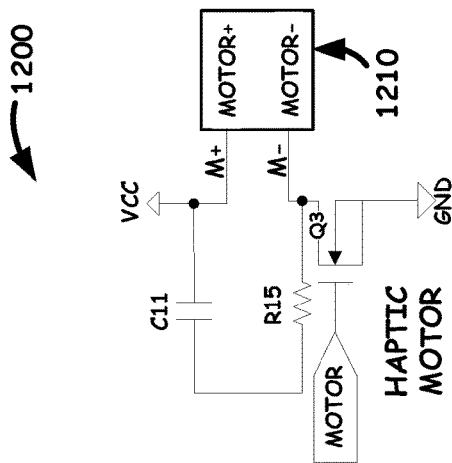
FIG. 12
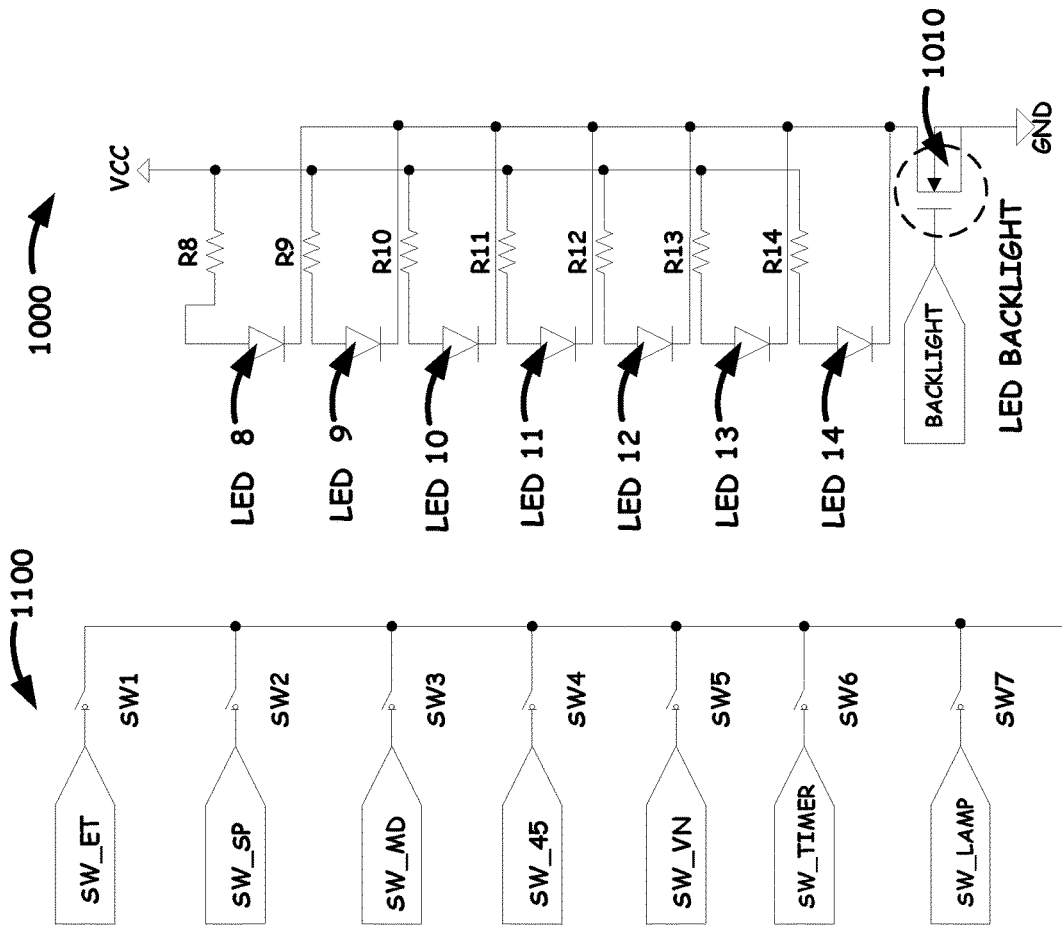
FIG. 10
FIG. 11

HANDHELD TESTING DEVICE INCLUDING MULTIPLE TIMERS

CROSS-REFERENCE TO RELATED APPLICATIONS

This application is a Continuation of U.S. patent application Ser. No. 16/564,989, filed on Sep. 9, 2019, which is a Continuation of U.S. patent application Ser. No. 15/642,623, filed on Jul. 6, 2017 (now U.S. Pat. No. 10,405,743, issued on Sep. 10, 2019), which is a Divisional of U.S. patent application Ser. No. 14/725,475, filed on May 29, 2015 (now U.S. Pat. No. 9,700,203, issued on Jul. 11, 2017), which claims priority to Provisional Application No. 62/051,380, filed on Sep. 17, 2014, the contents of all of which are incorporated herein in their entirety and for all purposes.

BACKGROUND OF THE INVENTION

Technical Field of the Invention

This invention relates generally to testing devices and more particularly to handheld testing devices including multiple timers.

Description of Related Art

Drug Evaluation Classification Exams are conducted by test administrators to assess substance use and impairment. Test administrators are many times law enforcement or medical personnel and test subjects are suspects or patients. When properly administered and documented, these evaluations can be used to assess the condition of a patient during initial medical triage, or to establish probable cause for an arrest or for a warrant to allow the gathering of evidence. Additionally, a properly administered and documented evaluation can be used as evidence at trial with respect to an offense for which alcohol or narcotic impairment is a required element of the offense.

Drug Evaluation Classification Exams include, but are not limited to Horizontal Gaze Nystagmus (HGN), Vertical Gaze Nystagmus (VGN), Lack of Ocular Convergence and Pupil evaluation. Gaze nystagmus refers to a jerking motion exhibited when the eye gazes to the side or upward. In the context of Drug Evaluation Classification Exams, consumption of certain other central nervous system depressants, inhalants or dissociative anesthetics, hinders the ability of the brain to correctly control eye muscles, therefore causing the jerk or bounce associated with gaze nystagmus. Central nervous system depressants, inhalants or dissociative anesthetics, may cause HGN. In addition, central nervous system depressants, inhalants or dissociative anesthetics drugs may cause VGN when taken in higher doses for that individual. Central nervous system depressants, inhalants or dissociative anesthetics drugs, as well as *cannabis* (marijuana), may also cause a lack of convergence. A subject lacks convergence if his eyes are unable to converge toward the bridge of his nose when a stimulus is moved inward. Pupil Evaluation under three lighting conditions, room light, low light and direct light is conducted to assist in determining drug categories. Certain drug categories affect the pupils, causing either dilation or constriction. This test can provide additional evidence of the possible influence of drugs on board the suspect.

Existing methods for conducting and documenting Drug Evaluation Classification Exams are subject to challenge with respect to the reliability of the administration and documentation of the test. Specifically, defense attorneys frequently attempt to challenge the admissibility of the test or argue to the finder of fact that the results of the Drug Evaluation Classification Exams were tainted by improper administration and documentation. In the medical context, an improperly conducted exam can lead to incorrect diagnosis and treatment decisions. Existing tools and methods for performing Drug Evaluation Classification Exams do not provide adequate guarantees of complete compliance with standards for administering the test. Further, existing tools and methods for performing of the Drug Evaluation Classification Exam tests do not provide adequate guarantees of reliable recording and documentation of test results.

BRIEF SUMMARY

Embodiments provide a handheld testing device for facilitating a Drug Evaluation and Classification Examination. One embodiment provides a handheld evaluation device including an image recorder configured to capture at least one of still images or video images, a function switch configured to operate the image recorder, a plurality of timers, each of which is associated with one or more portions of a substance evaluation protocol, and processing circuitry coupled to the image recorder, the function switch, and a plurality of actuators operatively associated with the plurality of timers. The processing circuitry is configured to initiate a first timer of the plurality of timers in response to detecting the activation of a first actuator of the plurality of actuators, activate the image recorder in response to detecting operation of the function switch, provide feedback associated with the first timer and at a plurality of predetermined times, determine completion of the first timer, and store in memory the at least one of still images or video images captured by the image recorder.

In some embodiments, the feedback is one selected from the group of tactile feedback, visual indications, or auditory indications, or each possible set or subset of tactile feedback, visual indications, and auditory indications. In some embodiments, the handheld device includes a haptic motor configured to provide tactile feedback associated with any one timer of the plurality of timers. In some embodiments, the handheld device includes a generally cylindrical-shaped housing including a first elongated surface, an opposed second elongated surface, a first end, and a second end. In some embodiments, the handheld device further includes at least one light source disposed on the first elongated surface, and an ultra-violet light source and a white-light source both disposed at or adjacent the first end.

In some embodiments, the function switch is a first function switch, and the processing circuitry is further configured to initiate a second timer of the plurality of timers in response to detecting activation of a second actuator of the plurality of actuators, activate the image recorder in response to detecting operation of a second function switch, determine completion of the first timer, and store in memory additional still images or video images captured by the image recorder. In some embodiments, the handheld device includes a communications port configured for electronic transfer of the still images or video images to an external device. In some embodiments, the plurality of actuators is backlit.

In some embodiments, the first timer is associated with a first portion of the substance evaluation protocol and is an Equal Tracking timer. In some embodiments, the plurality of actuators further includes a second actuator selectable to activate a second timer, wherein the second timer is associated with a second portion of the substance evaluation protocol and is a Smooth Pursuit timer. In some embodiments, the plurality of actuators further includes a third actuator selectable to activate a third timer, wherein the third timer is associated with a third portion of the substance evaluation protocol and is a Maximum Deviation timer. In some embodiments, the plurality of actuators further includes a fourth actuator selectable to activate a fourth timer, wherein the fourth timer is associated with a fourth portion of the substance evaluation protocol and is an Angle of Onset timer. In some embodiments, the plurality of actuators further includes a fifth actuator selectable to activate a fifth timer, wherein the fifth timer is associated with a fifth portion of the substance evaluation protocol and is a Vertical Nystagmus timer.

Another embodiment provides a handheld testing device for facilitating a Drug Evaluation and Classification Examination. The device includes a cylindrical housing having a longitudinal axis, the cylindrical housing including a first end and a second end opposite the first end along the longitudinal axis. The device includes a first light source proximal the first end on a first surface of the cylindrical housing, a camera positioned between the first light source and the second end on the first surface, the camera configured to capture at least one of still images or video images, and a second light source positioned between the camera and the second end on the first surface. The device includes a plurality of actuators located on a second surface of the cylindrical housing radially opposite the first surface, wherein one actuator of the plurality of actuators is configured to operate the camera and wherein another actuator of the plurality of actuators is configured to operate one of the first light source or second light source.

In some embodiments, the first light source includes a red light emitting diode. In some embodiments, the second light source includes a white light emitting diode. In some embodiments, the device further includes a plurality of timers, wherein each timer is associated with one or more subportions of the Drug Evaluation Classification Exam and configured for initiation via an actuator of the plurality of actuators.

The present disclosure is directed to apparatus and methods of operation that are further described in the following Brief Description of the Drawings, the Detailed Description of the Invention, and the claims. Various features and advantages of the present invention will become apparent from the following detailed description of the invention made with reference to the accompanying drawings.

BRIEF DESCRIPTION OF THE SEVERAL VIEWS OF THE DRAWING(S)

FIG. 1 is a view of a user-facing side of a handheld testing and timing device according to various embodiments of the present disclosure;

FIG. 2 is a view of a subject-facing side of a handheld testing and timing device according to various embodiments of the present disclosure;

FIG. 3 is a view of an end of handheld testing and timing device that includes multiple light sources is illustrated according to various embodiments of the present disclosure;

FIG. 4 is a user-facing view of a handheld testing and timing device according to various embodiments of the present disclosure;

FIG. 5 is a subject-facing view of a handheld testing and timing device according to various embodiments of the present disclosure;

FIG. 10 is a schematic diagram illustrating LED backlighting circuitry according to various embodiments of the present disclosure;

FIG. 11 is a schematic diagram illustrating a plurality of switches used to trigger various timers according to various embodiments of the present disclosure;

FIG. 12 is a schematic diagram illustrating a haptic motor and associated circuitry according to various embodiments of the present disclosure;

DETAILED DESCRIPTION OF THE INVENTION

Figure 6:
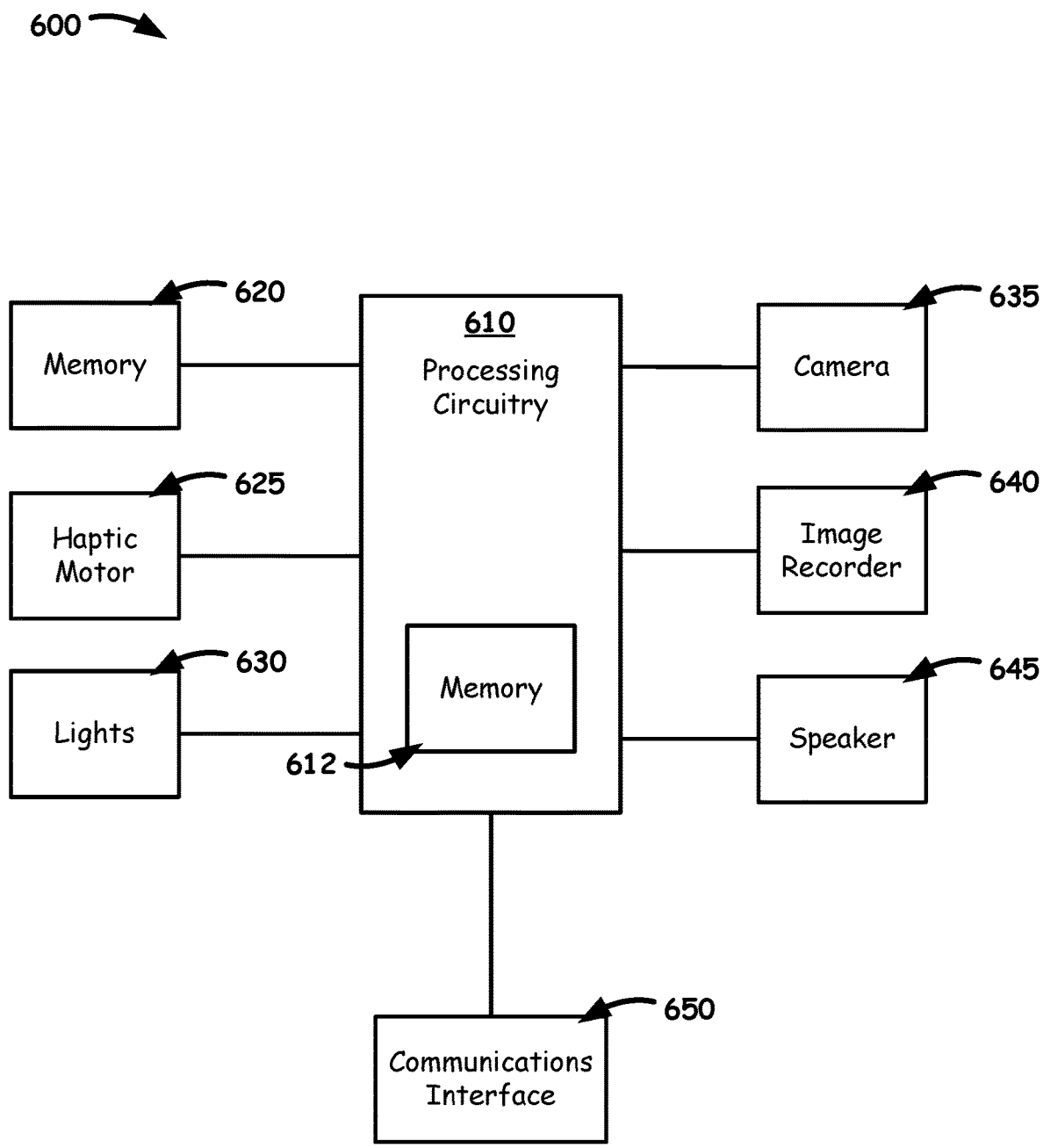
FIG. 6 is a block diagram illustrating a system including various components of a handheld testing and timing device, according to various embodiments of the present disclosure.

Various embodiments of the claimed testing and timing device include a generally cylindrical housing configured to be held in one hand of a user administering a Drug Evaluation Classification Exam. The testing and timing device includes a light source. To administer a Drug Evaluation Classification Exam, the user holds the testing device so that the light source is facing a test subject, and turns on the light. The user activates a series of timers, and begins moving the test device across the test subject's field of vision according to a test protocol. The series of timers trigger tactile indications that guide the user in properly conducting the Drug Evaluation Classification Exam.

In various embodiments, the series of timers includes an Equal Tracking timer that controls a first series of tactile feedback indications delineating sub-portions of an Equal Tracking portion of a nystagmus test, and a Smooth Pursuit timer that controls a second series of the tactile feedback indications delineating sub-portions of a Smooth Pursuit portion of the nystagmus test. The user can activate each of the timers by selecting one of multiple different buttons. In some embodiments the buttons are backlit, and flash to indicate the appropriate next button to select. In some embodiments, circuitry included in the testing and timing device prevent the user from selecting timer buttons in the wrong order.

Various embodiments also provide one or more fixed-interval timers that can be used by medical personnel to assist in performing medical assessments such as determining a test subject's pulse rate. Rather than requiring the user to continually check a watch or clock while counting the number of beats, the user can simply start a timer, and count the number of beats until the fixed-interval timer triggers an alert.

As used herein, unless otherwise indicated or required based on context, the term "Equal Tracking" refers to a prerequisite test used to determine whether a test subject's eyes follow an object simultaneously. A lack of equal tracking can indicate that a medical disorder or injury, and according to a resource guide published guidelines published by the National Highway Traffic, and Safety Administration (NHTSA), a Horizontal Gaze Nystagmus test should be discontinued if the Equal Tracking test reveals that the subject exhibits a lack of equal tracking.

The term "Horizontal Gaze Nystagmus (HGN)," as used herein, refers generally to assessing movement of a test subject's eyes as they attempt to follow a moving object side to side. The term "Vertical Gaze Nystagmus" refers to assessing movement of a test subject's eyes as they attempt to follow a moving object vertically (up and down). The term "Lack of Convergence" is when a test subject's eyes are unable to converge toward the bridge of their nose when a stimulus is moved inward. "Pupil Evaluation" under three lighting conditions, room light, low light and direct light is conducted to assist in determining drug categories.

An HGN test is designed to allow observation of the lack of smooth pursuit as the eye follows the object moving along a horizontal line in front of a test subject, and can be considered to be divided into a number of sub-tests, each of which has particular timing requirements: Equal Tracking, Smooth Pursuit, Maximum Deviation, and Forty-five Degree Onset. The Equal Tracking test, although technically a test performed prior to testing for nystagmus, is usually considered to be a part of the HGN test. An additional prerequisite test, Equal Pupil Size, is performed prior to checking for a nystagmus to determine if the subject's pupils are of equal size. If the pupils are not of equal size, a potential medical issue or injury is indicated, and HGN testing should be discontinued.

To check for a nystagmus during the Smooth Pursuit portion of a test, a user administering the HGN test moves an object slowly but steadily from the center of the subject's face towards the left ear. The left eye should smoothly follow the object, but if the eye exhibits nystagmus, the test administrator notes the clue as an indication of intoxication. The test administrator then checks the right eye.

During a Maximum Deviation portion of the HGN test, the user checks to see if a distinct and sustained nystagmus occurs at Maximum Deviation of the subject's eye from a center line of the test subject's view. Starting from the center of the test subject's face, the test administrator moves the object toward the left ear, bringing the eye as far over as possible, and holds the object there for four seconds. The test administrator notes the clue if there is a distinct and sustained nystagmus at this point. The test administrator holds the object at maximum deviation for at least four seconds to ensure that quick movement of the object did not possibly cause the nystagmus. The test administrator then checks the right eye. This is also referred to as "end-point" nystagmus.

During a Forty-five Degree Onset portion of the HGN test, the user conducting the test determines if the onset of nystagmus occurs prior to forty-five degrees. The test administrator moves the object at a speed that would take about four seconds for the object to reach the edge of the test subject's left shoulder. The test administrator notes this clue if the point or angle at which the eye begins to display nystagmus is before the object reaches forty-five degrees from the center of the test subject's face. The test administrator then moves the object towards the test subject's right shoulder. Generally, forty-five degrees from center is at the point where the object is in front of the tip of the subject's shoulder. As a rule of thumb, a person's blood alcohol concentration can be estimated by subtracting the angle of onset from 50 degrees. Therefore, a person with an angle of onset of nystagmus at 35 degrees has a blood alcohol concentration of approximately 0.15%

A Vertical Nystagmus test is used to check for vertical nystagmus by raising the object several inches above the subject's eyes. Vertical nystagmus is commonly interpreted as an indication of high doses of alcohol, other central nervous system (CNS) depressants or inhalants, and the consumption of the drug phencyclidine (PCP).

In some instances, a Lack of Convergence (LOC) test can be performed to determine whether a test subject's eyes are unable to converge toward the bridge of their nose when a stimulus is moved inward. When conducting the check for the LOC, the test administrator will begin the procedure by moving the stimulus in a circular motion in front of the subject's face while observing the subject's eyes to verify that they are tracking the stimulus. Then the test administrator will slowly move the stimulus in, toward the bridge of the subject's nose, stopping approximately, but no closer than two (2) inches from the bridge of the subject's nose. The test administrator will slowly move the stimulus to the subject's nose, stopping at the bridge of the nose. Normally a person's eyes should come together and cross (converge) as they track and stay aligned on a stimulus as it is moved in toward the bridge of their nose. Clinical research studies indicated that many normal non impaired people cannot converge to the bridge of their nose. However, most can converge to the minimum distance of approximately two inches from the bridge of the nose for a normal convergence response. By stopping the stimulus approximately, but no closer than two inches from the bridge of the nose, test administrator will be more proficient in identifying persons who may not be able to converge their eyes naturally and not impaired by central nervous system depressants, inhalants, dissociative anesthetics and *cannabis*.

In addition to the HGN and other tests, a Pupil Evaluation can be performed, a Pupil Evaluation is normally performed to assist in determining drug categories. The Pupil Evaluation is usually conducted under three lighting conditions: room light, low light and direct light is conducted. Certain drug categories affect the pupils, causing either dilation or constriction. This test can provide additional evidence of the possible influence of drugs on board the suspect.

Proper and reliable implementation of the tests described above can be important to ensure that accurate test results are achieved, for both legal and medical reasons. For example, in the law enforcement context, improper administration and documentation of a test can prevent the results of that test from being useful in court. In the medical diagnostic context, incorrectly performed tests can lead to misdiagnosis and improper treatment decisions.

Various embodiments disclosed herein can provide a standardized, handheld device, which can be used by law enforcement officers and medical personnel to properly administer and document Drug Evaluation Classification and other medical Examinations. The device can include a light source positioned in or on a housing, so that the test subject pupils may be examined. The device can also include a transducer, for example a haptic motor, configured to generate tactile feedback to indicate passage of a particular amount of time. For example, during a Dark Room/Near Total Darkness step of an exam, the test administrator should darken the room, wait 90 seconds, and the proceed with the examination. A 90 second fixed-interval timer can be used in conjunction with the haptic motor to provide tactile feedback to the user at the conclusion of a 90 second interval. Further embodiments of the device may provide for tactile feedback at other intervals controlled by various fixed-interval timers. For example, tactile feedback, such as a vibration, can be used to alert a user that a fixed interval of 15 seconds has elapsed during a direct light step of a pupil exam. The 90 and 15 second fixed-interval timers can be used to provide cues to a user administering a test to begin or end tests, thereby providing a reliable guide to the proper time passage of the standardized 90 seconds for the Dark Room/Near Total Darkness and 15 seconds Direct Light portion of the Drug Evaluation Classification Exam.

In addition to tactile feedback, a device according to various embodiments can also generate other types of feedback indicating the passage of a particular amount of time, such as visual indications, auditory indications, or some combination thereof. For example, one or more light sources capable of emitting, or being filtered to present, light of varying colors may be used; a white light colored light can be presented while performing a test, a red light can be presented to indicate that a test is in progress, and a green light can be presented to indicate that a test is complete.

By providing reliable measurement of time and cues to the passage of time in order to assure all interested parties that the test was conducted correctly, embodiments of the present invention may increase the reliability of test results and protect the results of the test from a legal challenge on the basis of an assertion improper timing of the standardized methods were not achieved during testing.

In some embodiments, additional features, such as an audio (e.g. microphone) or video recording device (e.g. camera) for capturing test subject response to the test, are included in handheld testing device. A memory may be included on the device for storing audio/video captured during the test. Additionally, in some embodiments, additional auditory cues, such as instructions to the test administrator or test subject, can be provided, possibly in a plurality of languages. Some embodiments of the present invention will also include interface components to allow the transfer of information to and from the handheld testing and timing device. Finally, in some embodiments, the invention is combined with a portable computing device, such as a smartphone.

Referring next to FIG. 1, various embodiments of a handheld testing and timing device 100 will be discussed. FIG. 1 shows user-facing side 101 of handheld testing an timing device 100, which includes a generally cylindrical housing 110 having a top portion 130 configured to house one or more light sources, and a bottom portion 140 configured as a glass breaker. Handheld testing and timing device 100 also includes a plurality of user selectable inputs illustrated as buttons 112-126. In at least some embodiments, some or all of buttons 112-126 can be backlit buttons. User selection of some or at least some of the buttons 112-126 activates various timers that can be used to alert the user when performing various tests, for example a nystagmus or other test performed as part of a Drug Evaluation Classification Exam.

As illustrated by FIG. 1, in at least one embodiment, ET button 112 can be selected, by itself or in conjunction with another button such as Function (fn) button 124, to activate either an Equal Tracking (ET) timer or a 15 second fixed-interval timer that can be used to time administration of a direct light examination. SP button 114 can be selected, by itself or in conjunction with another button such as fn button 124, to activate either a Smooth Pursuit (SP) timer, or a 30 second fixed-interval timer that can be used to assist a user in determining a subject's pulse rate. MD button 116 can be selected, by itself or in conjunction with another button such as fn button 124, to activate either a Maximum Deviation (MD) timer, or a 90 second fixed-interval Dark Room timer, which can be used to ensure that a test administrator waits long enough for a test subject's eyes to adjust to total room darkness. Forty-five degree button 118 can be selected to activate a Forty-five Degree timer. VN button 122 can be selected to activate a Vertical Nystagmus (VN) timer. Fn button 124 can be used in combination with other buttons or user selectable inputs to change a function associated with any particular button or combination of buttons. Tactile or other feedback indications can be presented at the conclusion of any interval or sequence of intervals being timed, and if desired also at the beginning of any interval or sequence of intervals.

Power button 126 can be used to change the power state of handheld testing and timing device 100, or to change a mode of operation. For example, a single press of Power button 126 can be used to toggle between a power on and power off state, between a standby state and an active state, or between other states. In some embodiments, each press of Power button 126 selects a next state in a sequence of states. For example a first press could be used to bring handheld testing and timing device 100 out of a standby mode and place it in a default mode, for example a "pre-programmed test" mode in which selecting buttons 112-116 activates corresponding test timers, and a second press of Power button 126 can be used to place handheld testing and timing device 100 into a "fixed timer" mode, in which selection of buttons 112-116 activates corresponding fixed timers. In some such modes, handheld testing and timing device 100 can automatically enter a standby or power off state after a predetermined amount of time without a button press.

Power button 126 can also be used, alone or in conjunction with other buttons or user inputs, to control various light sources (illustrated in subsequent figures) included in handheld testing and timing device 100. For example, selecting ET button 112 plus Power button 126 can turn on a light source used to conduct the Equal Tracking test. Similarly, selecting fn button 124, MD button 116, and Power button 126 in a predetermined sequence can illuminate light source used to conduct a Dark Room/Near Total Darkness step of an exam, and set MD button 116 to a fixed-timer mode in which selection of MD button 116 initiates a 90-second fixed timer.

In some embodiments, repeatedly pressing the power button cycles through each available light source. In other implementations, fn button 124 can be used to activate the light sources, or select which light source will be activated in response to pressing Power button 126.

In at least one embodiment, buttons 112-126 can be backlit buttons, with the backlight illuminating a border of the buttons, illuminating a center portion of the button, or illuminating button identifiers or text included on buttons 112-126. Backlighting buttons 112-126 can be used to facilitate a user's ability to find and activate a particular button in low-light situations. In at least one embodiment, backlit buttons 112-126 are visible to the user, but not to a test subject. This can be accomplished by using low-intensity backlighting, by slightly recessing illuminated portions of buttons 112-126, by screening, by using a polarized filter material over buttons 112-12, or using some other suitable method.

Referring next to FIG. 2, a subject-facing side 201 of handheld testing and timing device 100 shown in FIG. 1 is illustrated, and will be discussed according to various embodiments of the present disclosure. Subject facing side 201 includes focus light source 250, and second light source 210. Additional light sources (not illustrated) can also be included on subject-facing side 201, or on other portions of handheld testing and timing device 100. In some embodiments (not illustrated), focus light source 250 and second light source 210 can be located about the long surface of cylindrical housing 110 at a position other than the user or the subject-facing side 201 of handheld testing and timing device 100, on a top portion of handheld testing and timing device 100, or on a bottom portion of handheld testing and timing device 100.

Focus light source 250 can be illuminated by a user to enhance the visibility of the device, and presented to a test subject as a reference point in conjunction with one or more portions of a Drug Evaluation and Classification Examination. In at least one embodiment, focus light source 250 includes a single, red light emitting diode (LED) that generates a wavelength of approximately 633 nm at a brightness of approximately 50 mcd. In various embodiments, the number of LEDs can vary, as can the frequency or the brightness of focus light source 250. For example, focus light source 250 can be selected to produce light in any one or more portions of the visible spectrum, for example a light source that produces yellow, green, blue, or even white light source. The brightness of focus light source 250 can, in some embodiments vary from less than 50 mcd to 100 mcd or more. Furthermore, in some implementations, the brightness of focus light source 250 can be varied by a user to levels empirically determined by the user to be comfortable for a particular test subject. In many embodiments, however, the brightness is substantially fixed at the time of manufacture, and is not adjustable by the user.

Second light source 210 can be, for example, an ultraviolet (UV) exam lamp, which can be used for multiple investigatory purposes, including dark room exams and counterfeit detection, or a white exam lamp, which can be used to conduct a pupil-reaction examination or as a flashlight. Where second light source 210 is a UV exam lamp, second light source 210 can be implemented as one or more LED lamps that generate light having a wavelength of approximately 385 nm. In other embodiments where second light source 210 is a UV exam lamp, a UV LED that generates light having a wavelength of approximately 375 nm can be used. LEDs generating other UV spectrum wavelengths can also be used. In embodiments where second light source 210 is a white exam lamp, a white LED having a color temperature of about 3500K can be used. In other embodiments, LEDs having warmer or cooler, color temperatures are used. The brightness of the white exam lamp is, in at least one embodiment, approximately 6-10 lumens.

Referring next to FIG. 3, an end portion of handheld testing and timing device 100, which includes multiple light sources is illustrated and discussed according to various embodiments of the present disclosure. As illustrated in FIG. 3, the end portion is discussed from the perspective of top portion 130, however, the same principles can be used to implement embodiments in which the end portion is incorporated into bottom portion 140 (FIGS. 1 and 2).

As illustrated, top portion 130 includes housing 310, first additional light source 322, second additional light source 324, and lens 320. In at least one embodiment, first additional light source 322 can be a UV light source, similar to the UV exam lamp discussed with respect to second light source 210. Second additional light source 324 can be a white light source, similar to the white exam lamp discussed above with reference to second light source 210. Lens 320 can be a single lens constructed of a material that is substantially transparent to one or both of the frequencies of light generated by first additional light source 322 and second additional light source 324. In other embodiments, lens 320 can include multiple lenses or lens portions (not illustrated), with different lenses or lens portions having different light transmission properties. For example, one lens or lens portion can be constructed to be more transparent to UV light, while a second lens or lens portion is constructed of a material that is more transparent to white light, or vice versa. Lens 320, or some portion thereof, may be constructed to achieve desired light transmission properties through use of various known materials, with or without various known coatings. Additionally, an adjustment bezel or slider switch (not specifically illustrated) similar to those used in conventional flashlights can be included to allow focal adjustment first additional light source 322, second additional light source 324

FIGS. 4 and 5 show user-facing side 401 and subject-facing side 501 of a handheld testing and timing device 400 according to various embodiments of the present disclosure.

Handheld testing and timing device 400 includes housing 410, tactical end 440, key 430, a plurality of user selectable inputs illustrated as buttons 412-426, primary light source 550, secondary light source 520, tertiary light source 530, camera 510, and communications port 540.

In at least one embodiment buttons 412-426 are placed on user-facing side 401. Some or all of buttons 412-426 can be backlit in one or multiple different colors. In various embodiments, the backlighting in the keys can be turned on and off, or placed under control of a processor to provide visual feedback to a user. Similar to the buttons described with respect to FIG. 1, user selection of buttons 412, 414, 416, 418, and 422, alone or in conjunction with function button 424, can initiate activation of various timers used to alert the user, or operator, regarding the performance of various tests, including tests that are part of a Drug Evaluation Classification Exam. User selection of buttons 412, 414, and 416, alone or in conjunction with function button 424, can initiate activation of various fixed timers, which can also be used to assist a user in timing portions of a Drug Evaluation and Classification Exam, or to aid the user in performing various medical evaluations, such as a pulse rate measurement.

In at least some embodiments, the functionality of each button does not change based on a device state, and activating particular buttons in particular sequences will always result in the same button behavior. In other implementations, buttons 412-426 can be configured to provide different functionality in different states of operation. In some implementations, power button 426 can be used, by itself or in conjunction with other buttons 412-425, to turn on or turn off handheld testing and timing device 400, or to change a power or operational state of handheld testing and timing device 400. For example, power button 426 can be used to toggle between a full power and a sleep state. In various embodiments, when in a sleep state, function button 424 can be used in conjunction with power button 426 to place handheld testing and timing device 400 into either 1) an Evaluation state, in which buttons 412-422 are configured to activate test timers used in conducting a Drug Evaluation Classification Exam; or 2) a Medical Exam state, in which buttons 412-416 are configured to activate fixed-duration timers, instead of activating test timers.

User-facing side 401 of handheld testing and timing device 400 also includes camera button 425, which can be used by itself or in conjunction with one or more of buttons 412-424 and 426 to activate camera 510. In some embodiments, camera 510 is capable of capturing either or both single images and videos. In at least one implementation, camera 510 can be activated by pressing camera button 425, which also illuminates secondary source 520 or tertiary source 530 to aid in providing sufficient light for image capture. In some cases, camera button 425 can be used to start and stop video capture by camera 510. In other embodiments pressing camera button 425 can cause camera 510 to capture a snapshot. Function button 424 can be used in conjunction with camera button 425 to toggle between a video and a still image mode.

In at least one embodiment, primary light source 550, secondary light source 520, tertiary light source 530, camera 510, and communications port 540 are located on subject-facing side 501 of handheld testing and timing device 400. Primary light source 550 is, in at least one embodiment, similar in construction and use to focus light source 250 (FIG. 2). Secondary light source 520 and tertiary light source 530 are, in at least one embodiment, a UV light source and a white light source similar in construction and use to first additional light source 322 (FIG. 3) and second additional light source 324 (FIG. 3). Any or all of the various light sources can be located in positions other than those explicitly illustrated, without departing from the spirit and scope of the present disclosure.

Communications port 540 can be a universal serial bus (USB) port, and Ethernet port, or any other suitable communication port that allows transfer of data and information, including captured still images, video images, sound, or recorded test data to or from handheld testing and timing device 400. Communications port 540 can also provide a way to program embodiments of handheld testing and timing device 400 that include a programmable processor. The use of communications port 540 can also allow insertion of a memory device that can be used for external storage of recorded information. In addition to, or in place of, communications port 540, handheld testing and timing device 400 can be equipped with wireless communications circuitry, for example Bluetooth circuitry (not explicitly illustrated).

Referring next to FIG. 6, a block diagram illustrating a system 600 including various components of a handheld testing and timing device, according to various embodiments of the present disclosure. System 600 includes processing circuitry 610 having internal memory 612, memory 620, Haptic motor 625, light sources 630, camera 635, microphone 640, speaker 645, and communications interface 650.

Processing circuitry 610 can include a programmable processor, such as a microcontroller, central processing unit (CPU), etc., or an application-specific integrated circuit (ASIC) or programmable logic array (PLA), such as a field programmable gate array (FPGA), designed to implement the functions performed by system 600, such as control, data capture, tactile and visual feedback, and sound output. Memory 612 can be used alone or in conjunction with memory 620 to store data and instructions to be executed by processing circuitry 610.

Haptic motor 625 can be controlled by processing circuitry 610 to provide tactile feedback to a user. Light sources 630 can include both button backlights, focus sources, white-light sources, UV light sources, and other light sources used to assist in the performance of medical diagnosis and Drug Evaluation Classification Examinations. Camera 635 can be used to record images of a test subject's performance on various portions of Drug Evaluation Classification Examinations, field sobriety tests, a test subject's condition, and other information that can be used to assist in diagnosing a test subject's medical condition. Microphone 640 can be used to record a verbal exchange between a user and a test subject. For example, microphone 640 can be used to help establish what was or was not communicated to a test subject during a Drug Evaluation Classification Examination, or to establish what the test subject said. Speaker 645 can be used to provide audible output from system 600, which can be used as audible feedback during testing, to play-back pre-recorded instructions to a test subject, or the like. Communications interface 650 can be a wired or wireless communications interface adopting any suitable currently known electronic communication protocol to allow information and data to be passed to and from system 600. In at least some embodiments, communications interface 650 can allow communications via computer network.

In some embodiments, various portions of system 600 can be used to capture testing data during a time when the test administrator is conducting a Drug Evaluation Classification Exam. For example, camera 635 can be used to record video of the subject's eyes during a test. The combination of a light sensor associated with a camera, and one or more of the light sources 630 can further be used to measure a distance between a handheld implementation of system 600 and the subject's face. In some embodiments, a distance from system 600 to the face of the test subject can be subsequently calculated by comparing a recorded distance between photographed features of the test subject's face to subsequent measurements of the face of the subject. Some embodiments may record a verification of angular movement with respect to the test subject's face, for example using the combination of motion data recorded by an accelerometer (not illustrated) included in the handheld device and either actual or inferred distance measurements.

In addition, in one embodiment during, before or after some portion of a test or sub-test, a GPS unit (not illustrated) included in the device or in communication with the device, can be used to record the GPS coordinates of a location at which the test was administered.

Figure 7:
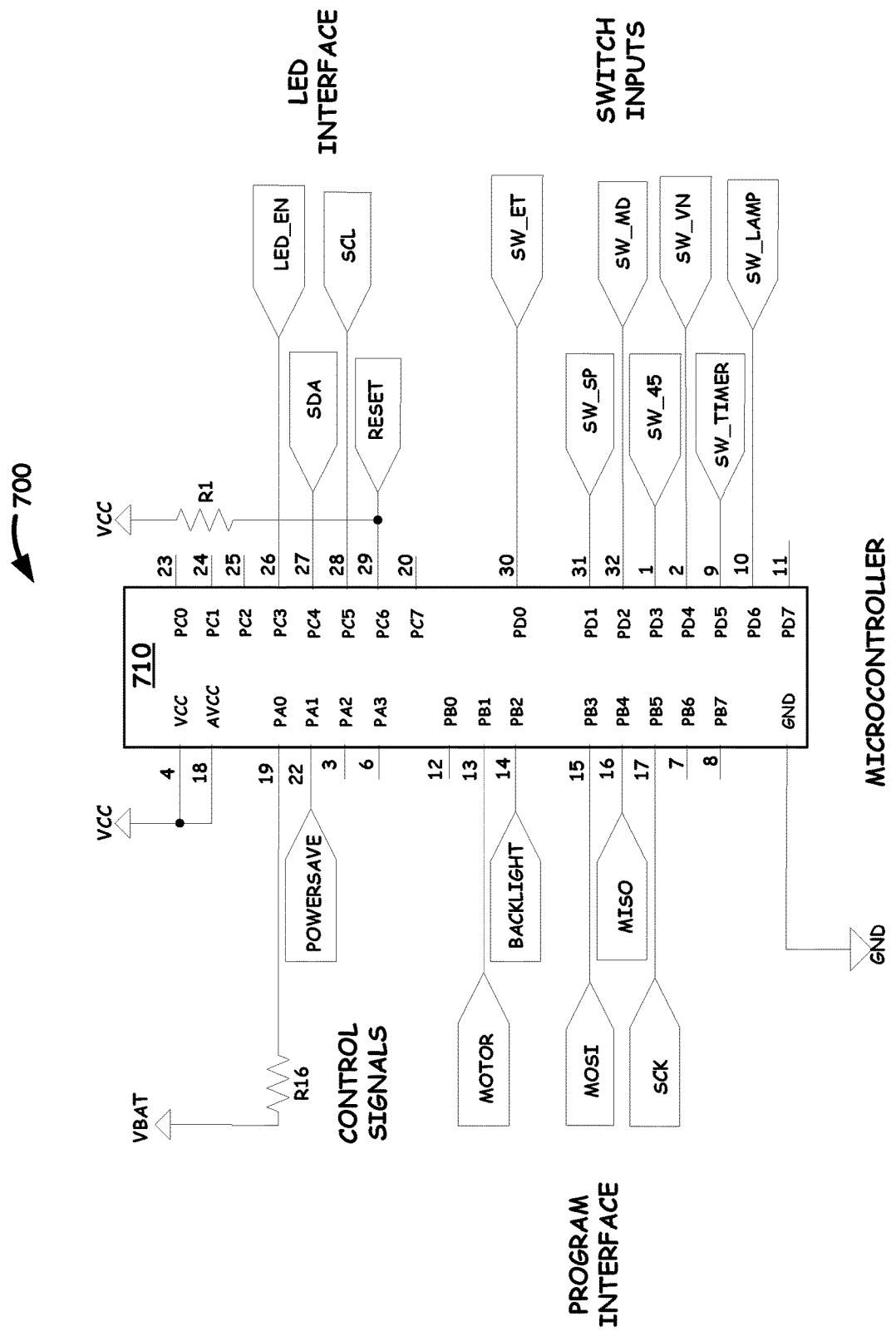
FIG. 7 is a schematic diagram illustrating processing circuitry, including a microcontroller, according to various embodiments of the present disclosure.

Referring next to FIG. 7, processing circuitry 700, including a microcontroller 710, is illustrated and discussed according to various embodiments of the present disclosure. Processing circuitry 700 can include a programmable microcontroller, a general purpose processor, discrete logic gates, firmware including a computer executable program of instructions for use with a microcontroller or other processor, or some combination of these and other components. Microcontroller 710 as illustrated in FIG. 7, can be, for example, an 8 bit RISC microprocessor such as an ATtiny48™ manufactured by Atmel®, which includes various types of onboard memory including Flash memory used to store program information; Static Random Access Memory (SRAM), which is volatile memory used to store data and register files; and non-volatile Electrically Erasable Programmable Read Only Memory (EEPROM) used for store data. Microcontroller 710 can also include one or more onboard clock systems and various registers and control outputs used to control various connected devices. Other types of microcontrollers and processors can be used without departing from the spirit and intent of the present disclosure.

As shown in FIG. 7, microcontroller 710 is connected to a DC voltage source VBAT, and to regulated power supply voltages VCC. Microcontroller 710 controls light emitting diodes (LEDS) or other light sources connected to Serial Bus Clock Line (SCL) on pin 28, serial Bus Data Input/Output Line (SDA) on pin 27, and an LED enable line connected to an Analog to Digital (ADC) input on pin 26. A reset input is connected at pin 29.

Microcontroller 710 is connected to a number of switch inputs, which when activated result in initiation of various timers. For example, when signal SW_ET is received, an Equal Tracking timer can be started. Similarly, receiving an SW_SP signal can trigger a Smooth Pursuit timer, receiving an SW_MD signal can trigger a Maximum Deviation timer, receiving an SW_VN signal can trigger a Vertical Nystagmus timer, receiving an SW_45 signal can trigger a 45 degree timer, and an SW_Timer signal can be used to cycle through one or more fixed-interval timers. SW_Lamp signal can be used to cycle through the available light sources, with an initial light source being activated the first time the SW_Lamp signal is received, a next light source activated the next time an SW_Lamp signal is received, and so on, until all available light sources have been cycled through, and receipt of the SW_Lamp signal turns off the last light source, but does not turn on the initial light source until a subsequent SW_Lamp signal is received.

A haptic motor or other tactile feedback device can be triggered using a Motor signal provided from pin 13. A Backlight control signal can be provided via pin 14. Microcontroller 710 can be programmed using Master Out Slave In (MOSI) data line at pin 15, Master In Slave out (MISO) data line at pin 16, and a serial clock (SCK) input on pin 17.

Figure 8:
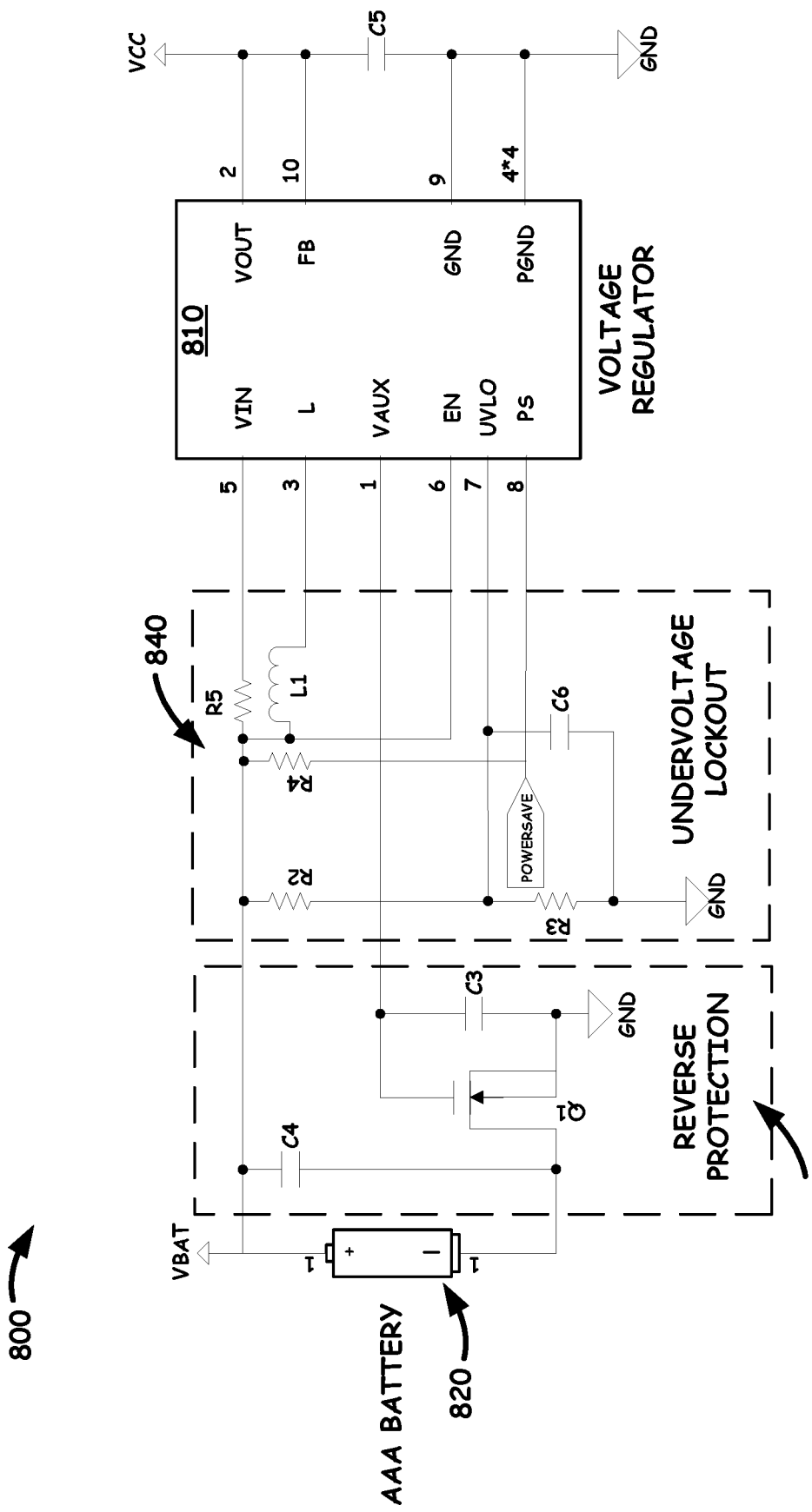
FIG. 8 is a schematic diagram illustrating power circuitry according to various embodiments of the present disclosure.

Referring next to FIG. 8, power circuitry 800 used in a handheld testing and timing device is illustrated and discussed according to various embodiments of the present disclosure. Power circuitry 800 includes voltage regulator 810, battery 820, reverse protection circuitry 830, and undervoltage lockout circuitry 840. Reverse protection circuitry 830 prevents damage a user from inadvertently causing damage by inserting battery 820 with its polarity reversed. Undervoltage lockout circuitry 840 prevents a low voltage condition from causing erratic or unpredictable results by assuring that operation is allowed only if battery 820 is providing sufficient voltage. Voltage regulator 810 is common voltage regulator such as the TPS61201DRC™ Low Input Voltage Synchronous Boost Converter, by Texas Instruments®

Figure 9:
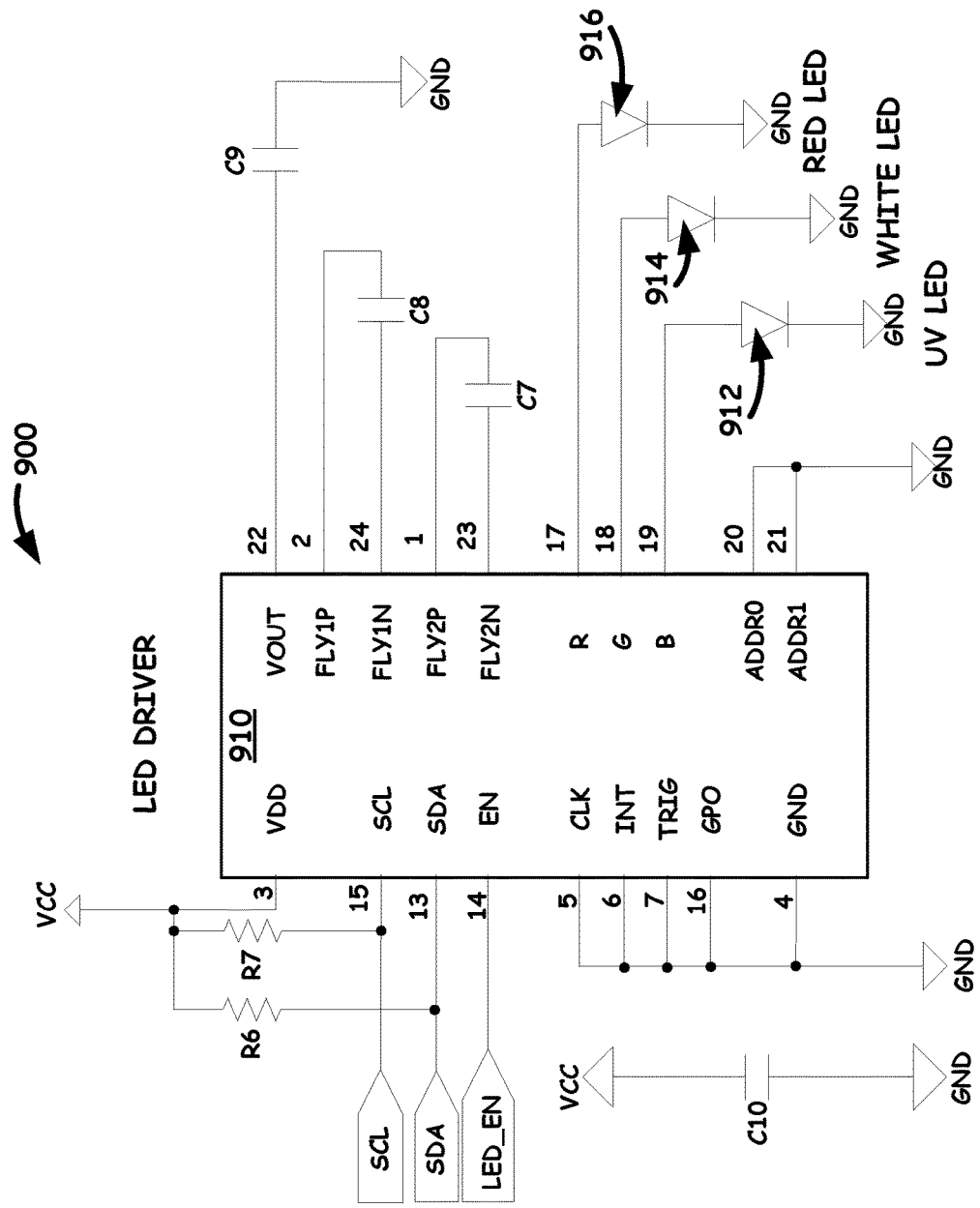
FIG. 9 is a schematic diagram illustrating light emitting diode (LED) driver circuitry according to various embodiments of the present disclosure.

Referring next to FIG. 9, light emitting diode (LED) driver circuitry 900 is illustrated and discussed according to various embodiments of the present disclosure. LED driver circuitry 900 can, in one embodiment include a programmable, three channel LED driver 910, such as the LP5521™ by Texas Instruments®. As illustrate in FIG. 9, Serial Bus Clock Line (SCL) from microcontroller 710 (FIG. 7), serial Bus Data Input/Output Line (SDA) from microcontroller 710 (FIG. 7), and the LED enable line from microcontroller 710 (FIG. 7) are connected to LED driver 910 to provide control signals for illuminating light sources such as UV LED 912, White LED 914, and Red LED 916 under control of various timers implemented using microcontroller 710. In various embodiments, Red LED 916 can be used as a focal point for a test subject, UV LED 912 can be used for various investigative purposes, including dark room examination, and White LED 914 can be used for pupil examination, as a flashlight, or for other investigative and medical diagnostic purposes.

Referring next to FIG. 10, switch circuitry 1000 is illustrated and discussed according to various embodiments of the present disclosure. In at least one embodiment, a series of switches is backlit by individual LEDs. In at least one embodiment, a single backlight switch 1010 is used to turn the power to the backlit LEDs on or off. In some embodiments, the backlight switch can be opened and closed repeatedly, causing all of the LEDs used to provide backlighting to flash, thereby providing visual feedback to a user of the handheld testing and timing device. In some embodiments, however, separate switches (not illustrated) can be provided for each individual LED, or for a combination of fewer than all of the LEDs, thereby indicating to a user the proper next button in a series of buttons to press during a Drug Evaluation and Classification Exam. Furthermore, one or more of the LEDs can emit light of a different color than other LEDs included in the handheld testing and timing device.

Referring next to FIG. 11 a schematic diagram illustrating switch circuitry 1100 is illustrated and discussed according to various embodiments of the present disclosure. Switch circuitry 1100 includes a plurality of switches SW1-SW7 used to generate used by microcontroller 710 (FIG. 7) to trigger various timers or to illuminate a particular light source. Switch SW1 is used to generate signal SW_ET; switch SW2 is used to generate signal SW_EP; switch SW3 is used to generate signal SW_MD; switch SW4 is used to generate signal SW_45; switch SW5 is used to generate signal SW_VN; SW6 is used to generate signal SW_Timer; and switch SW7 is used to generate signal SW_Lamp.

In the illustrated embodiment, the handheld testing and timing device can remain in a lower power state, and use of the power button 126 (FIG. 1) can be used to cycle through the various available light sources. In other embodiments, more or fewer switches and buttons can be used. Furthermore, processing circuitry 700 (FIG. 7) can be configured to perform different actions based on different closing sequences of switches SW1-SW7.

Referring next to FIG. 12, haptic motor circuitry 1200 is illustrated and discussed according to various embodiments of the present disclosure. Haptic motor circuitry 1200 includes haptic motor 1210, which is controlled by transistor Q3 based on Motor signal generated by microcontroller 710 (FIG. 7). Haptic motor 1210 can be used to provide tactile feedback under control of a timer implemented by microcontroller 710.

Figure 13A:
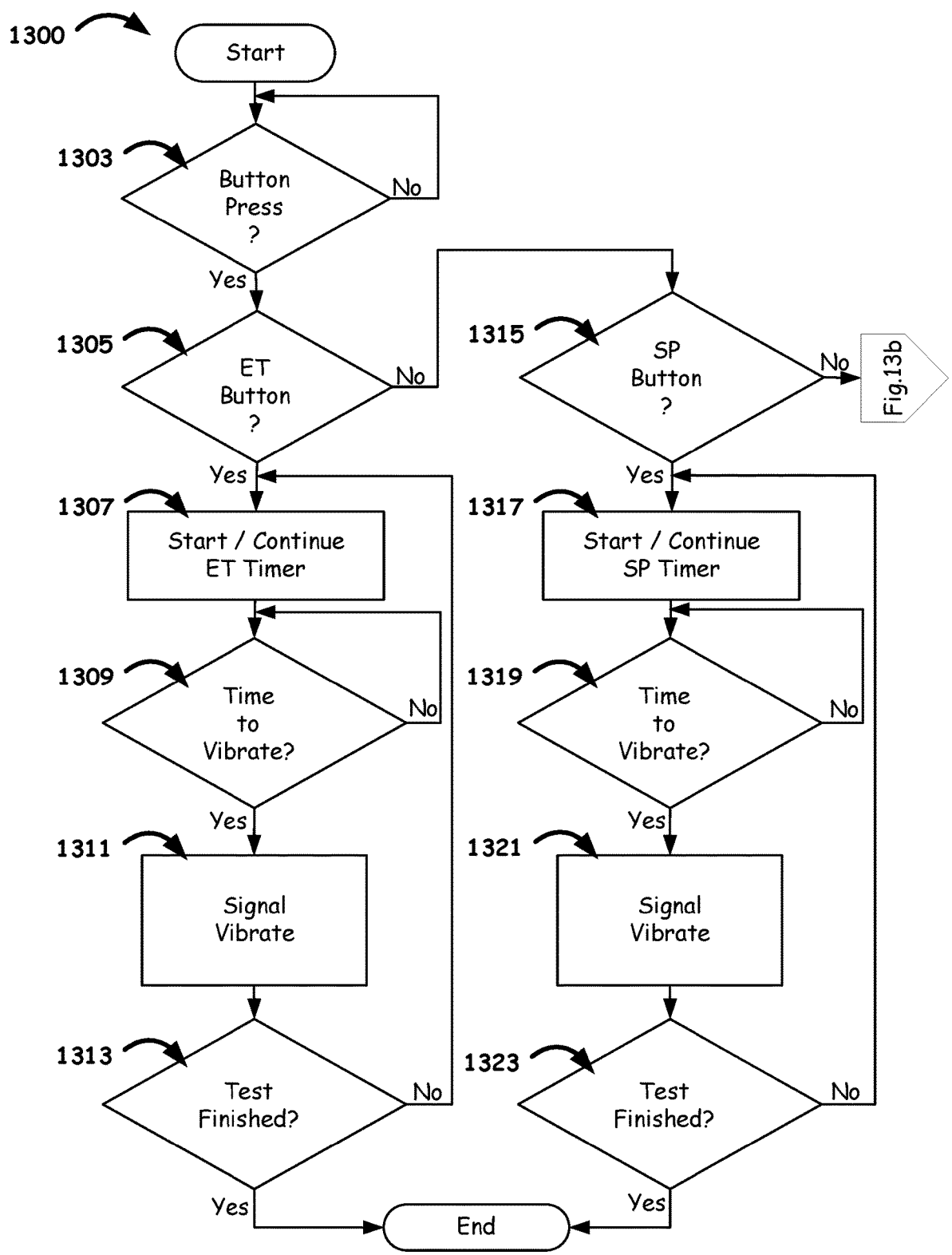
FIGS. 13a-13c are schematic diagrams illustrating a method of controlling a plurality of timers according to various embodiments of the present disclosure.
Figure 13B:
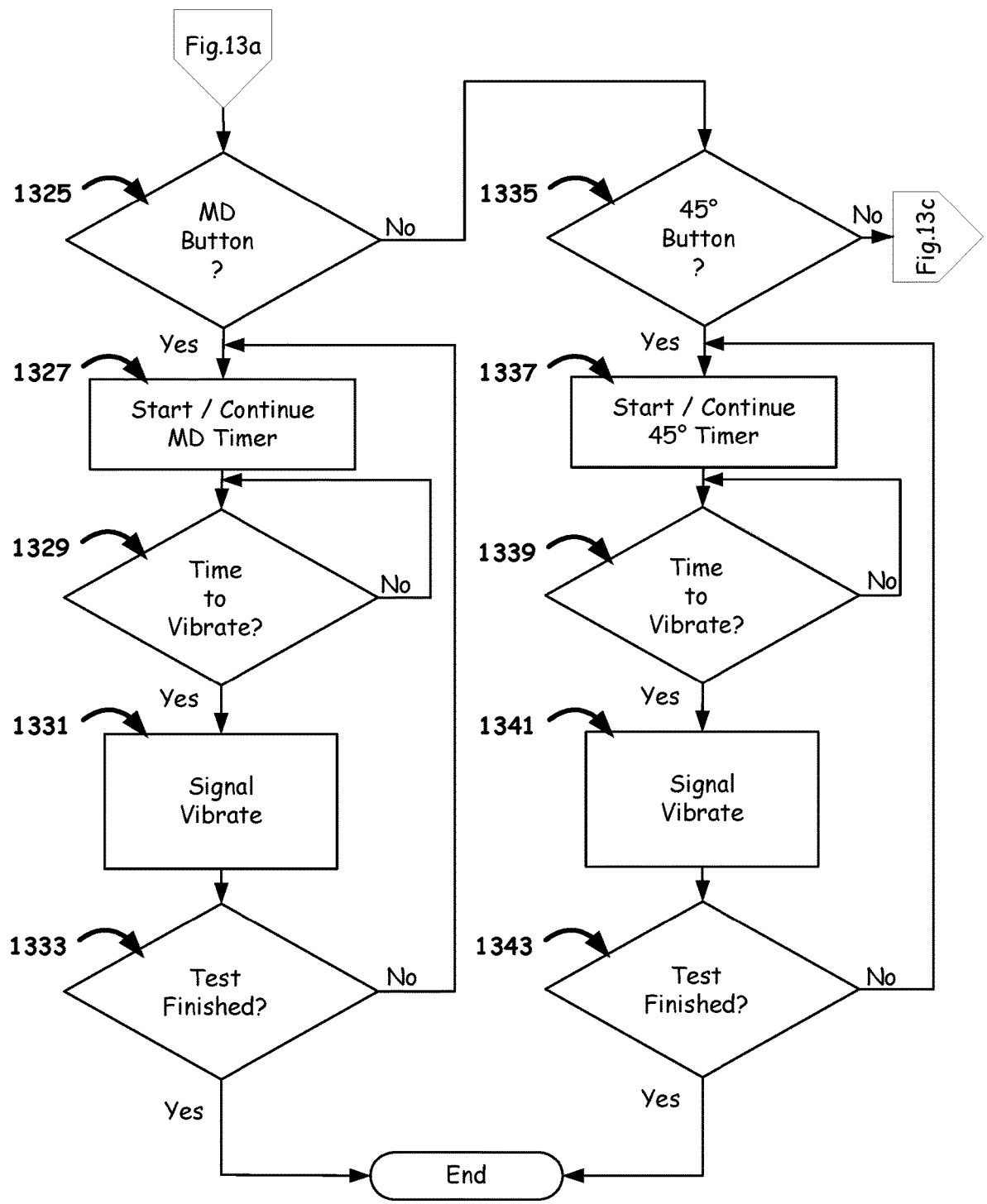
Figure 13C:
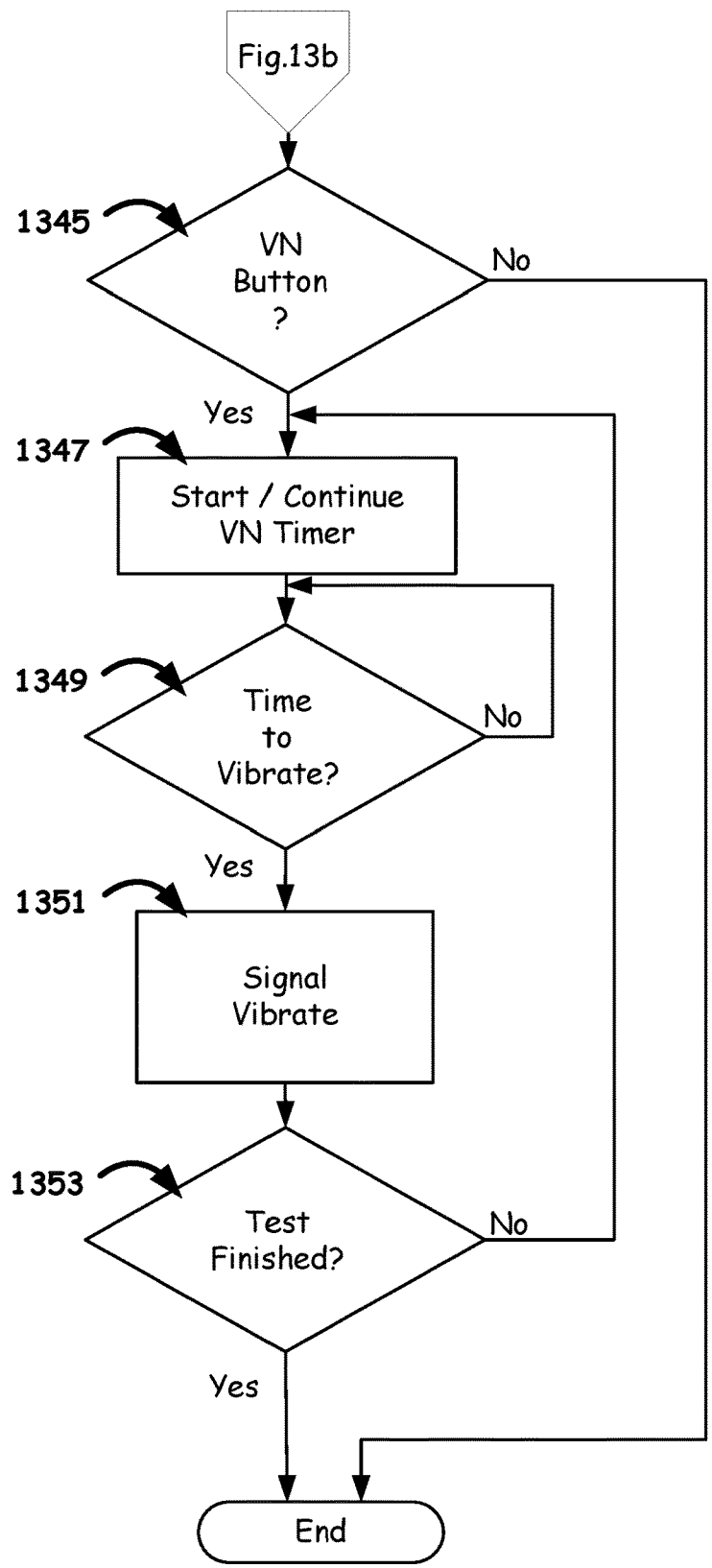

Referring next to FIGS. 13*a*-13*c* a method 1300 of controlling a plurality of timers will be discussed according to various embodiments of the present disclosure. In general, method 1300 illustrates an embodiment in which processing circuitry determines which timer button has been pressed, and then generates triggers tactile or other feedback to the user indicating that a portion of a test associated with the selected timer has been completed, has started, or is about to start. This feedback can be used by a test administrator, or user, as an indication that a particular action associated with the test should be performed. Although tactile feedback is the focus of the illustrated embodiments, other types of feedback, including various combination of audible, visible, and tactile feedback, are contemplated; unless otherwise specifically required by the language of the appended claims, explicitly excluded in the specification, or otherwise required by context, other types of feedback can be substituted for tactile feedback without departing from the spirit or scope of the disclosure. Some embodiments can, however, employ tactile feedback preferably to audible feedback, to avoid confusing, distracting, or otherwise giving unnecessary feedback that is easily observable by a test subject.

Method 1300 begins at block 1303, where a check is made to determine if a timer button has been pressed. If a timer button has not been pressed, method 1300 can simply wait, and continue to check for a button press. If the result of the decision made at block 1303 indicates that a timer button has been pressed, a check is made to determine whether an Equal Tracking (ET) button has been pressed.

In at least one embodiment, determining whether or not an ET button has been pressed includes determining whether a predetermined sequence of buttons have been pressed. For example, in embodiments where a handheld testing and timing device is programmed or otherwise configured to activate an ET timer only if a function button is pressed concurrently with an Equal Tracking button, the determination at block 1305 will indicate that an ET button has been pressed if the Function button and the ET button are pressed concurrently, but will otherwise indicate that the ET button has not been pressed. In embodiments where pressing the ET button in a first mode of operation will activate the Equal tracking timer and pressing the ET button in a second mode of operation activates a different timer, activation of the ET button in the first mode would register as a press of the ET button, while activation of the ET button in the second mode would not register as a press of the ET button for purposes of block 1305. Other button combinations than those explicitly described above can also be used consistent with the teachings set forth herein.

As illustrated in block 1307, in response to registering a press of the ET button at block 1305, an Equal Tracking (ET) timer can be started. As illustrated by block 1309, a check is made to determine whether the ET timer has reached a "Feedback time". In at least one embodiment, an ET timer is programmed to initiate user feedback at various predetermined intervals, and to provide feedback at the beginning of one of one or more of the intervals, at the end of one or more intervals, or some combination thereof. For example as illustrated at block 1309, a check can be made to determine if 2 seconds have elapsed from a time the ET timer was started. If it is determined that 2 seconds have elapsed, a signal is sent from the processing circuitry implementing the ET counter to control an output device to generate a feedback indication, as shown by block 1311. As illustrated by block 1313, a check is made to determine whether the feedback indication generated at block 1311 is the last feedback indication specified by the ET timer. If so, method 1300 ends, and the processing circuitry included in the handheld testing and timing device awaits another button press.

If, however, the feedback indication generated at block 1311 is not the last feedback indication to be produced by the ET timer, method 1300 returns to block 1307, and continues executing the ET timer, by waiting for the proper time to generate feedback at block 1309, generating the feedback at block 1311, and testing for completion of the ET timer sequence at block 1313.

In some embodiments, blocks 1307-1313 loop, as follows, until the ET timer sequence has completed: A) Wait 2 seconds to give the user time to position the handheld device at or slightly above eye level at the center of the test subject's face, then generate a feedback indication to signal the beginning of the ET test; B) wait 2 seconds, while the user moves the handheld device from the center of the test subject's face towards the test subject's left ear and checks to make sure that the test subject's eyes track the target light source equally, then generate feedback indicating that the user should be in position and ready to perform the next portion of the test; C) wait 2 seconds while the user moves the handheld device back towards the center of the test subject's face, then generate feedback indicating that the user should be in a center position and ready to perform the next portion of the test; D) wait 2 seconds, while the user moves the handheld device from the center of the test subject's face towards the test subject's right ear and checks to make sure that the test subject's eyes track the target light source equally, then generate feedback indicating that the user should be in position and ready to perform the next portion of the test; E) wait 2 seconds while the user moves the handheld device back to the center of the test subject's face while checking for equal tracking of the test subject's eyes, then generate feedback indicating that the user should be in position and ready to perform the next portion of the test; repeat portions B-E.

In the above example, after going through a first iteration including portions A-E and repeating test portions B-E, blocks 1307-1313 will have looped through 9 iterations, after which block, 1313 will determine that the ET test has been completed. The feedback indications can vary for different portions of the test. For example, the first feedback indication generated by the ET timer, and each of the tactile indications given when the handheld device is held at the centerline of the test subject's vision, can be multi-pulse or patterned tactile indications, while remaining feedback indications can be single-pulse tactile indications. In some embodiments, tactile and audible indications can be combined for some of the feedback indications. For example, the first and the final feedback indication can be a combination of audible and tactile indications. In some embodiments, the initial feedback indication can include pre-recorded audio instructions directing the test subject to, for example, "Keep your head still, and follow the light with your eyes."

Referring again to block 1305, if a determination has been made at block 1305 that the button pressed is not the ET button, a check is made at block 1315 to determine if the button pressed is the Smooth Pursuit (SP) button. If it is determined at block 1315 that the SP button has been pressed, the SP timer is started at block 1317. As illustrated by block 1319, if the SP timer indicates that it is time to generate feedback, a signal is generated at block 1321 and used to control a haptic motor or other type of transducer, a speaker, or a light source to provide feedback indicators in accordance with the SP timer. As illustrated by block 1323, a check is performed to determine whether the SP test has completed, and that there are no further feedback indicators to be generated according to the SP timer. As with the ET timer, the SP timer can be configured to provide multiple feedback indicators at various points throughout the SP test.

In some embodiments, blocks 1317-1323 loop, as follows, until the SP timer sequence has completed: A) Wait 2 seconds to give the user time to position the handheld device at or slightly above eye level at the center of the test subject's face, then generate a feedback indication to signal the beginning of the SP test; B) wait 2 seconds, while the user moves the handheld device from the center of the test subject's face towards the test subject's left ear and checks to make sure that the test subject's eyes track the target light source equally, then generate feedback indicating that the user should be in position and ready to perform the next portion of the test; C) wait 2 seconds while the user moves the handheld device back towards the center of the test subject's face, then generate feedback indicating that the user should be in a center position and ready to perform the next portion of the test; D) wait 2 seconds, while the user moves the handheld device from the center of the test subject's face towards the test subject's right ear and checks to make sure that the test subject's eyes track the target light source equally, then generate feedback indicating that the user should be in position and ready to perform the next portion of the test; E) wait 2 seconds while the user moves the handheld device back to the center of the test subject's face while checking for equal tracking of the test subject's eyes, then generate feedback indicating that the user should be in position and ready to perform the next portion of the test; repeat portions B-E.

In the above example, after going through a first iteration including portions A-E and repeating test portions B-E, blocks 1317-1323 will have looped through 9 iterations, after which block, 1323 will determine that the SP test has been completed. The feedback indications can vary at different portions of the test. For example, the first feedback indication generated by the SP timer, and each of the tactile indications given when the handheld device is held at the centerline of the test subject's vision, can be single-pulse tactile indications, while remaining feedback indications can be multi-pulse or patterned tactile indications. In some embodiments, tactile and audible indications can be combined for some of the feedback indications. For example, the first and the final feedback indication can be combined visual and tactile indications.

Referring again to block 1315, if a determination has been made at block 1303 that a button has been pressed, but the determination at block 1305 indicates that the button pressed is not the ET button and the determination at block 1315 indicates that the button pressed is not the SP button, a check is made at block 1325 to determine if the button pressed is the Maximum Deviation (MD) button. If it is determined at block 1315 that the MD button has been pressed, the MD timer is started at block 1327. As illustrated by block 1329, if the MD timer indicates that it is time to generate a feedback indication, a signal is generated at block 1331 and used to control a haptic motor or other type of transducer, a speaker, or a light source to provide feedback indicators in accordance with the MD timer. As illustrated by block 1333, a check is performed to determine whether the MD test has completed, and that there are no further feedback indicators to be generated according to the MD timer. Similar to the ET and SP timers, the MD timer can be configured to provide multiple feedback indicators at various points throughout the MD test.

In some embodiments, blocks 1327-1333 loop, as follows, until the MD timer sequence has completed. In various embodiments, the "time to vibrate" decision illustrated at block 1329 need not be a constant time for each iteration of blocks 1327-133. For example, during a first iteration, through block 1329, block 1329 can wait for 2 seconds, during a second iteration block 1329 can wait for 4 seconds, while third and subsequent iterations can each have varying wait periods determined according to parameters of the MD test. In at least one embodiment, the MD timer iterates through blocks 1327-1333 as follows: A) Wait 2 seconds to give the user time to position the handheld device at or slightly above eye level at the center of the test subject's face, then generate a feedback indication to signal the beginning of the MD test; B) wait 2 seconds, while the user moves the handheld device from the center of the test subject's face towards the test subject's left ear, bringing the test subject's eyes as far over as possible, then generate feedback indicating that the user should hold the device in position until the next feedback indication is generated; C) wait 4 seconds, while the user holds the handheld testing and timing device in position and checks for a distinct nystagmus at maximum deviation, then generate a feedback indication alerting the user that he should begin the next sub-portion of the MD test; D) wait 2 seconds while the user moves the handheld device back towards the center of the subject's face, then generate feedback indicating that the user should be in a center position and begin moving the device towards the test subjects right ear; E) wait 2 seconds, while the user moves the handheld device from the center of the test subject's face towards the test subject's right ear, bringing the test subject's eyes as far over as possible, then generate feedback indicating that the user should hold the device in position until the next feedback indication is generated; F) wait 4 seconds, while the user holds the handheld testing and timing device in position and checks for a distinct nystagmus at maximum deviation, then generate a feedback indication alerting the user that he should begin the next sub-portion of the MD test; G) wait 2 seconds while the user moves the handheld device back towards the center of the subject's face, then generate feedback indicating that the user should be back in the center position; repeat portions B-G.

In the above example of an MD timer, after going through a first iteration including portions A-G and repeating test portions B-G, blocks 1327-1333 will have looped through 13 iterations, after which block, 1333 will determine that the ET test has been completed. The feedback indications can vary at different portions of the test. For example, the first feedback indication generated by the ET timer, and each of the tactile indications given when the handheld device is held at the centerline of the test subject's vision, can be multi-pulse tactile indications, while other feedback indications can be single pulse or patterned tactile indications. In some embodiments, tactile and audible indications can be combined for some of the feedback indications.

Referring again to block 1325, if block 1325 determines that the MD button has not been pressed, a check is made at block 1335 to determine if the button pressed is the 45 Degree (45*a*) button. If it is determined at block 1335 that the 45° button has been pressed, the 45° timer is started at block 1337. As illustrated by block 1339, if the 45° timer indicates that it is time to generate feedback, a signal is generated at block 1341 and used to control a haptic motor or other type of transducer, a speaker, or a light source to provide feedback indicators in accordance with the 45° timer. As illustrated by block 1343, a check is performed to determine whether the 45° test has completed, and that there are no further feedback indicators to be generated according to the 45° timer. As with the ET timer, the 45° timer can be configured to provide multiple feedback indicators at various points throughout the 45° test sequence.

In some embodiments, blocks 1337-1343 loop, as follows, until the 45° timer sequence has completed: A) Wait 2 seconds to give the user time to position the handheld device at or slightly above eye level at the center of the test subject's face, then generate a feedback indication to signal the beginning of the 45° test; B) wait 4 seconds, while the user moves the handheld device from the center of the test subject's face towards the test subject's left shoulder and checks for onset of nystagmus prior to 45 degrees, where 45 degrees is typically the point at which the handheld device reaches the tip of the test subject's shoulder, then generate feedback indicating that the handheld device should be at the 45 degree position; C) wait 2 seconds while the user positions the handheld device back at the center of the test subject's face, then generate feedback indicating that the user should begin moving the handheld device towards the test subject's right shoulder; D) wait 4 seconds, while the user moves the handheld device from the center of the test subject's face towards the test subject's right shoulder and checks for onset of nystagmus prior to 45 degrees, then generate feedback indicating that the handheld device should be at the 45 degree position. In at least one embodiment, the 450 test sequence is determined to be complete at this point.

In the above example, after completing portions A-D, blocks 1337-1343 will have looped through 4 iterations. In various embodiments, the 45° timer sequence can include additional iterations. Furthermore, in some embodiments rather than waiting 4 seconds at block 1339 to generate a tactile or other type of feedback indication, the 45° timer can be programmed to generate feedback indications periodically, for example every second, thereby aiding a user in determining a proper speed at which to move the handheld device during the 45° test sequence.

Referring again to block 1335, if it is determined at block 1335 that the 45° button has not been pressed, a check is made at block 1345 to determine whether the button pressed is the vertical nystagmus (VN) button. If it is determined at block 1345 that the VN button has been pressed, the VN timer is started at block 1347. As illustrated by block 1349, if the VN timer indicates that it is time to generate feedback, a signal is generated at block 1351 and used to control a haptic motor or other type of transducer, a speaker, or a light source to provide feedback indicators in accordance with the VN timer. As illustrated by block 1353, a check is performed to determine whether the VN test has completed, and that there are no further feedback indicators to be generated according to the VN timer. As with the other timers discussed herein, the VN timer can be configured to provide multiple feedback indicators at various points throughout the VN test sequence.

In some embodiments, blocks 1347-1353 loop, as follows, until the VN timer sequence has completed: A) Wait 2 seconds to give the user time to position the handheld device at eye level, centered on the test subject's face, then generate a feedback indication to signal the beginning of the VN test; B) wait 2 seconds, while the user moves the device from a position directly in front of the test subject to a position in front of and above the test subject to focus the test subjects eyes as far upward as possible, then generate feedback indicating that the handheld device should be at uppermost position; C) wait 4 seconds while the user holds the handheld device at the uppermost position and checks for nystagmus, then generate feedback indicating that the user should begin moving the handheld device towards the center of the test subjects face; D) wait 2 seconds, while the user moves the handheld device back to the center of the test subject's face then generate feedback indicating that the handheld device should be back at the center position. In at least one embodiment, the VN test sequence is determined to be complete at this point. In the above example, after completing portions A-D, blocks 1347-1353 will have looped through 4 iterations. In various embodiments, the VN timer sequence can include additional iterations.

Referring again to block 1345, if it is determined at block 1345 that the VN button has not been pressed, method 1300 ends. In various embodiments, additional checks for additional timer buttons can be implemented, although not specifically illustrated in FIGS. 13a-13c.

Figure 14A:
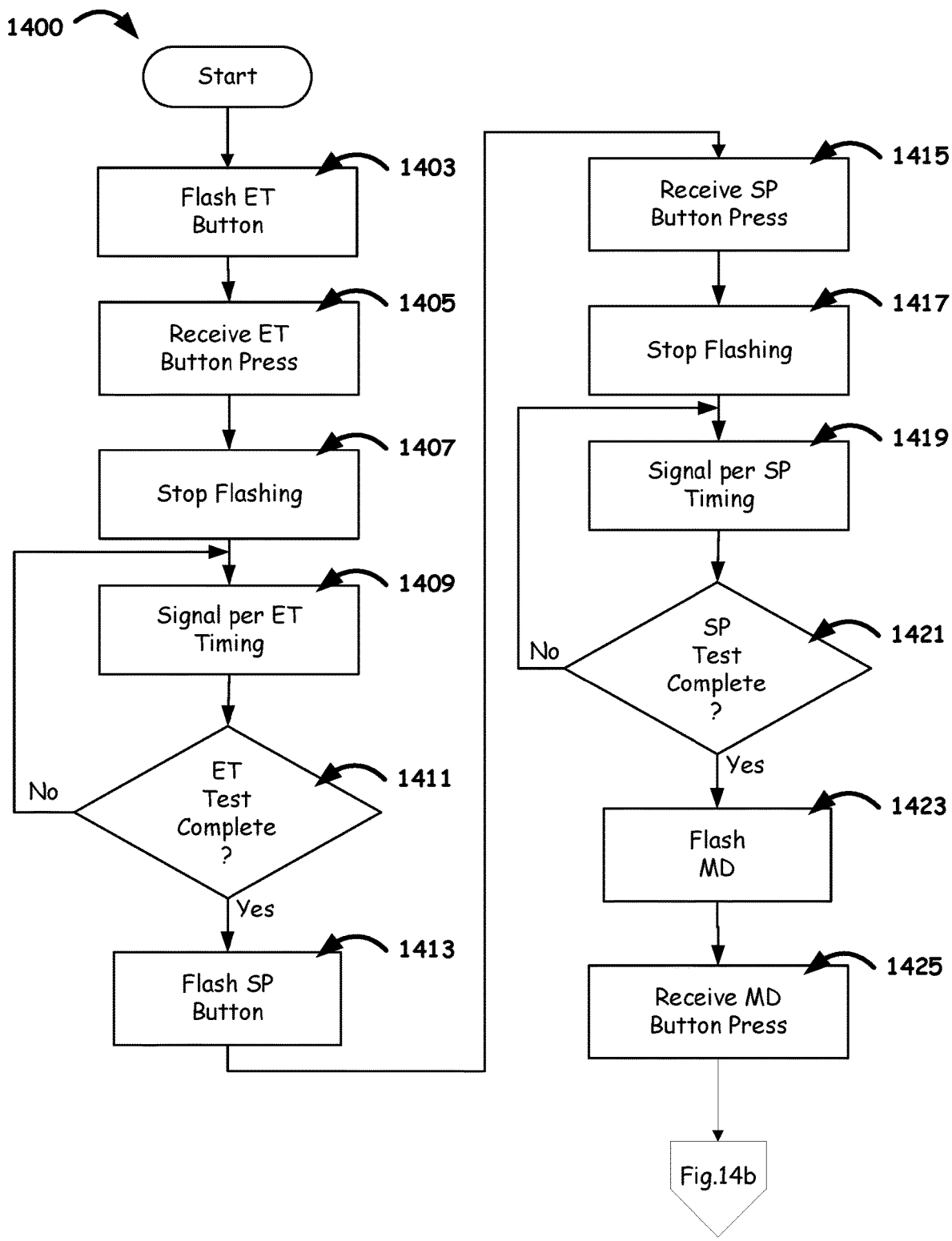
FIGS. 14a-14b are schematic diagrams illustrating a method of signaling a proper order of timer initiation to a user of a handheld testing and timing device according to various embodiments of the present disclosure.
Figure 14B:
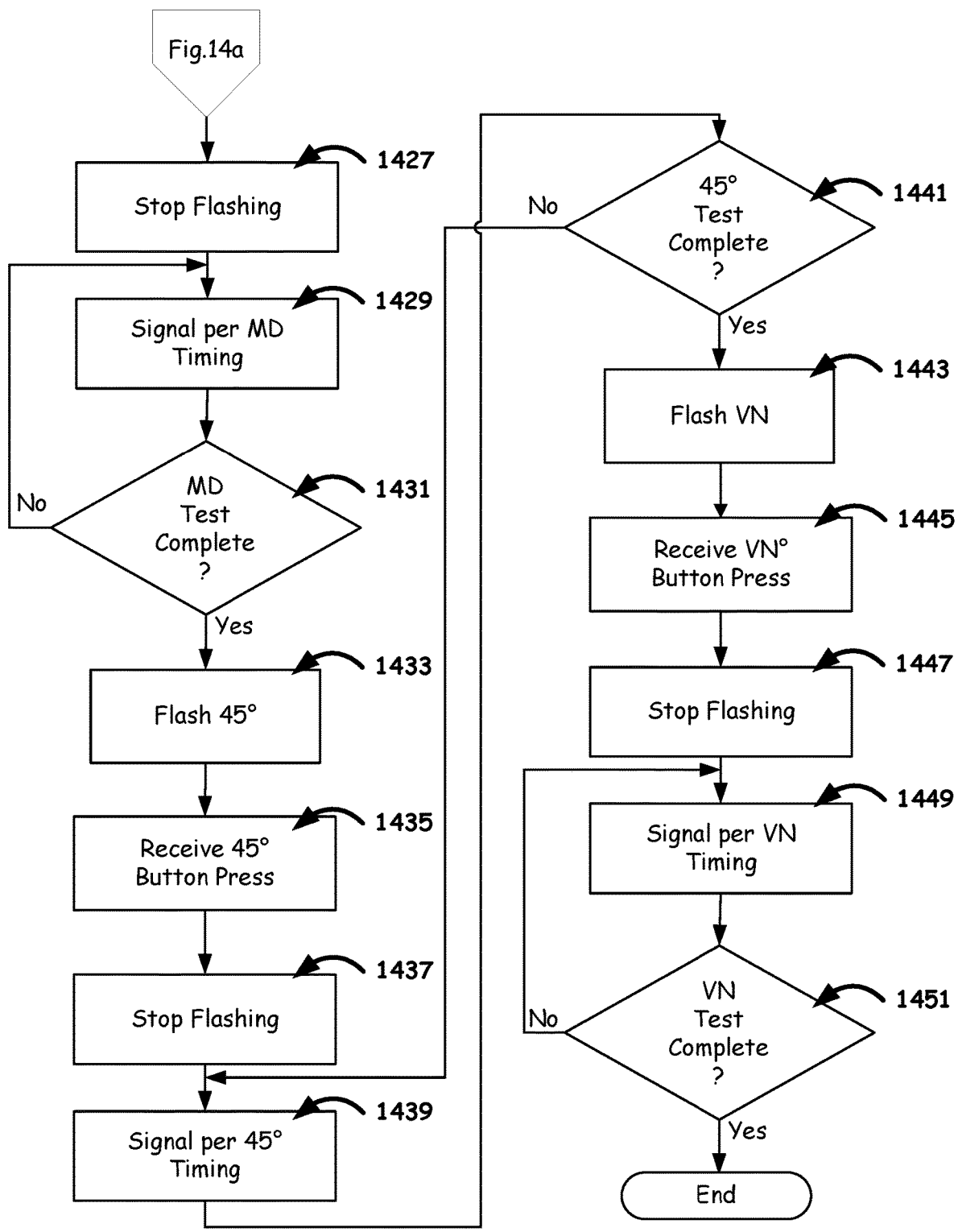

Referring next to FIGS. 14a-14b a method 1400 of signaling a proper order of timer initiation is illustrated and discussed according to various embodiments of the present disclosure. Method 1400 begins by flashing a first timer button in a sequence of buttons to be pressed to complete a Drug Evaluation Classification Examination, as illustrated at block 1403. Note that although the following example describes a particular Drug Evaluation Classification Examination, other timer and button sequences tailored for use with other tests can also be implemented using the techniques described herein. In at least one embodiment, the button flash illustrated at block 1403 can be implemented by flashing an LED associated with the next button to be pressed, where the next button to be pressed can correspond to a particular timer. Flashing the next button to be pressed can aid a user administering a test to properly implement the test by performing sub-tests in a prescribed sequence or order. Flashing a button, as illustrated by block 1403, can include flashing a light source in proximity to the button, for example flashing an indicator next to the proper button.

In at least one embodiment the first button to be pressed as part of, or preliminarily to, performing a Drug Evaluation Classification Examination is the ET button. The ET button and its associated timer have been previously discussed. In response to flashing the ET button, as illustrated by block 1403, processing circuitry can register an ET button press, as illustrated by block 1405. In response to receiving the ET button press, the flashing of the ET button is discontinued at block 1407, and feedback indications are generated in accordance with the ET timer sequence, as illustrated by block 1409. In some embodiments, stopping the flashing can include steady illumination of the previously flashing indicator light.

A check is performed at block 1411 to determine if the ET timer sequence is complete. If the ET timer sequence is not yet complete, method 1400 returns to block 1409 as many times as needed until the ET test is complete. Once the ET test is complete, as indicated by block 1411, the next button in the sequence of test buttons can be flashed. In addition to flashing the next button to be pressed, additional indications of a completed test can also be presented to a user. For example, after pressing a button but before a test is complete, a green indicator can be illuminated next to the currently active button. A green indicator can be illuminated to indicate that a test associated with a particular button has been completed.

In the illustrated example, the next button to be pressed is the SP button. Consequently, the SP button is flashed at block 1413. A button press of the SP button is registered at block 1415, and flashing of the SP button is stopped, as illustrated by block 1417. As illustrated by block 1419, feedback indications, for example tactile feedback indications provided by a haptic motor, are provided according the SP timer. A check is made at block 1421 to determine if the SP test is complete. If not, method 1400 returns to block 1419, and signaling in accordance with the SP timer continues. If block 1421 indicates that the SP test is complete, the next button in the sequence is flashed.

In the illustrated example, the next button to be pressed after the SP button is the MD button. Therefore, the MD button is flashed at block 1423. A button press of the MD button is registered at block 1425, and flashing of the MD button is stopped, as illustrated by block 1427. As illustrated by block 1429, feedback indications are provided according the MD timer sequence. A check is made at block 1431 to determine if the MD test is complete. If not, method 1400 returns to block 1429, and signaling in accordance with the MD timer continues. If block 1431 indicates that the MD test is complete, the next button in the sequence is flashed.

In the illustrated example, the next button to be pressed after the SP button is the 450 button. Therefore, the 45° button is flashed at block 1433. A button press of the 45° button is registered at block 1435, and flashing of the 45° button is stopped, as illustrated by block 1437. As illustrated by block 1439, feedback indications are provided according the 45° timer sequence. A check is made at block 1441 to determine if the 45° test is complete. If not, method 1400 returns to block 1439, and signaling in accordance with the 45° timer continues. If block 1441 indicates that the 45° test is complete, the next button in the sequence is flashed.

In the illustrated example, the next button to be pressed after the MD button is the VN button. Therefore, the VN button is flashed at block 1443. A button press of the VN button is registered at block 1445, and flashing of the VN button is stopped, as illustrated by block 1447. As illustrated by block 1449, feedback indications are provided according the VN timer sequence. A check is made at block 1451 to determine if the VN test is complete. If not, method 1400 returns to block 1449, and signaling in accordance with the VN timer continues. If block 1451 indicates that the VN test is complete, method 1400 ends, because there are no further timer buttons that need to be pressed in sequence for the illustrated example.

Figure 15:
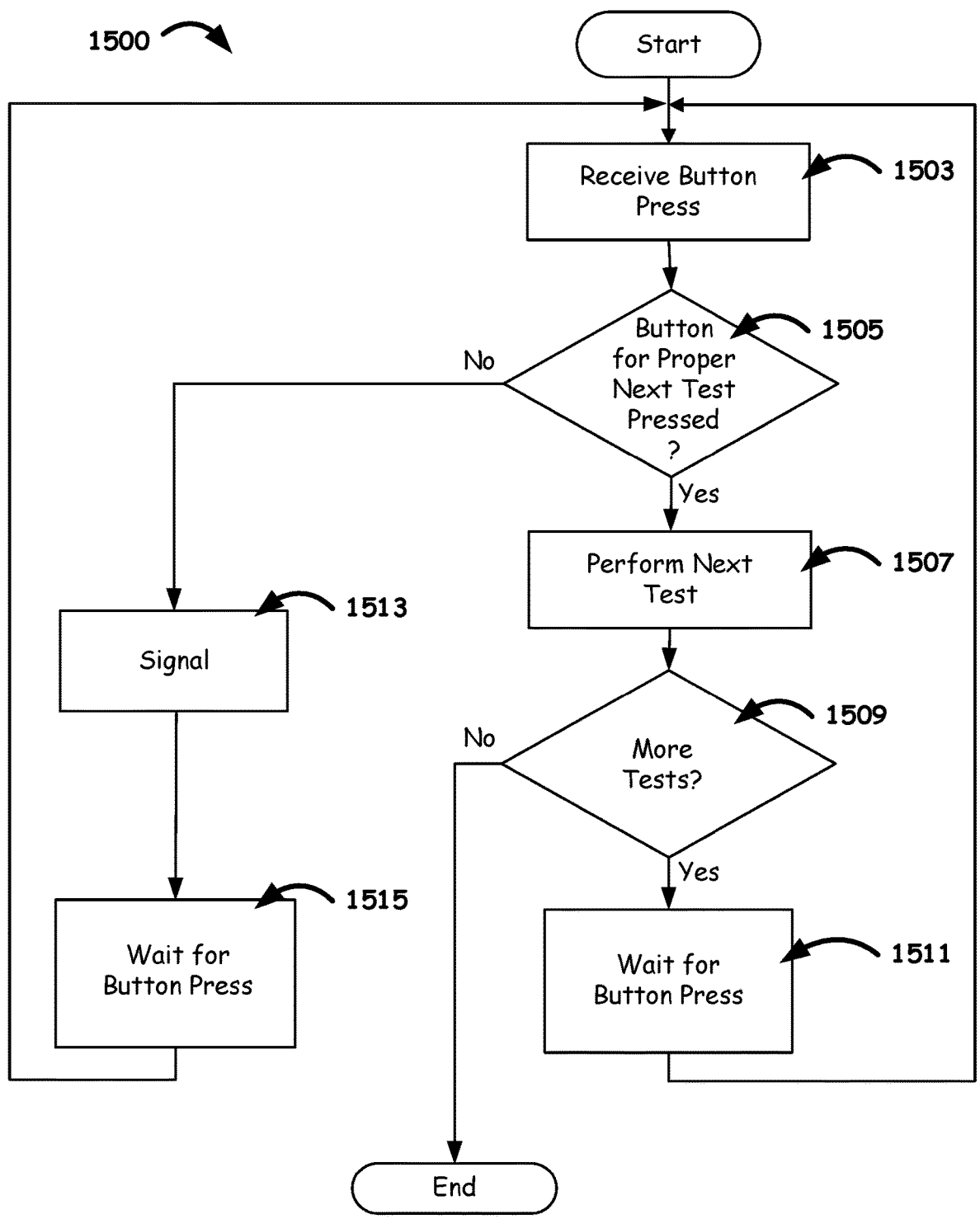
FIG. 15 is a schematic diagram illustrating a method of preventing out-of-order selection of timers according to various embodiments of the present disclosure.

Referring next to FIG. 15 a method 1500 of preventing out-of-order selection of timers will be discussed according to various embodiments of the present disclosure. In various embodiments, method 1500 can be used in conjunction with, or in place of method 1400, which was described with reference to FIG. 14. In general, method 1500 can be used to ensure that a group of tests or subtests having particular timing requirements are conducted in a preferred or required order. For example, in at least one embodiment, to conduct a Drug Evaluation Classification Exam, the following sub-tests are often performed in a particular order: an equal tracking (ET) test, a smooth pursuit (SP) test, a maximum deviation (MD) test, a 45 degree (45°) test, and a vertical nystagmus (VN) test. Each of the sub-tests has its own timing requirements associated with particular buttons or button combinations included on a handheld testing and timing device, as described herein. In some instances the order of some of the tests can be varied without serious consequence, but it is often desirable to have users perform the tests in a set order to avoid potential mistakes in test administration. In some embodiments, the ET should be performed before any of the other tests, because the ET test can serve as an indicator of a medical condition that could indicate the remaining tests should not be conducted.

Method 1500 begins by receiving a button press, as illustrated by block 1503. As illustrated by block 1505, a check is made to determine whether the button pressed is the proper next button in a predetermined sequence of buttons. If it is determined at block 1505 that the wrong button was pressed, a feedback indicator, such as a buzz or a vibration, can be generated to notify the user that the incorrect button was pressed, as illustrated by block 1513. After signaling the user at block 1513, method 1500 proceeds to block 1515 to await another button press.

If the check at block 1505 indicates that the proper next button was activated by the user, the timer associated with the proper next button is activated, and the test associated with the timer is performed, as illustrated by block 1507. Upon completion of the test being performed, a check is made at block 1509 to determine whether more tests remain to be completed. If there are more tests or sub-tests to be completed, method 1500 waits for a button press, as illustrated by block 1511. If it is determined at block 1509 that there are no more tests or sub-tests to be completed, method 1500 ends.

As explained above, embodiments of the present disclosure provide tools for reliably conducting and documenting Drug Evaluation Classification Exams, which in turn can reduce challenges to the reliability of the administration and documentation of tests conducted in the field.

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item.

As may also be used herein, the terms "processing module", "processing circuit", "processor", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may be, or further include, memory and/or an integrated memory element, which may be a single memory device, a plurality of memory devices, and/or embedded circuitry of another processing module, module, processing circuit, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the figures. Such a memory device or memory element can be included in an article of manufacture.

One or more embodiments of an invention have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality. To the extent used, the flow diagram block boundaries and sequence could have been defined otherwise and still perform the certain significant functionality. Such alternate definitions of both functional building blocks and flow diagram blocks and sequences are thus within the scope and spirit of the claimed invention. One of average skill in the art will also recognize that the functional building blocks, and other illustrative blocks, modules and components herein, can be implemented as illustrated or by discrete components, application specific integrated circuits, processors executing appropriate software and the like or any combination thereof.

The one or more embodiments are used herein to illustrate one or more aspects, one or more features, one or more concepts, and/or one or more examples of the invention. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

While the transistors in the above described figure(s) is/are shown as field effect transistors (FETs), as one of ordinary skill in the art will appreciate, the transistors may be implemented using any type of transistor structure including, but not limited to, bipolar, metal oxide semiconductor field effect transistors (MOSFET), N-well transistors, P-well transistors, enhancement mode, depletion mode, and zero voltage threshold (VT) transistors.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

While particular combinations of various functions and features of the one or more embodiments have been expressly described herein, other combinations of these features and functions are likewise possible. The present disclosure of an invention is not limited by the particular examples disclosed herein and expressly incorporates these other combinations.

What is claimed is:

1. A handheld evaluation device comprising:
a cylindrical housing having a longitudinal axis;
an image recorder positioned on the cylindrical housing and configured to capture at least one of still images or video images;
a function switch configured to operate the image recorder;
a plurality of timers, each of which is associated with one or more portions of a substance evaluation protocol, the substance evaluation protocol including the performance of a plurality of nystagmus tests; and
processing circuitry coupled to the image recorder, the function switch, and a plurality of actuators operatively associated with the plurality of timers, wherein each actuator of the plurality of actuators is backlit, the processing circuitry configured to
initiate a first timer of the plurality of timers in response to detecting activation of a first actuator of the plurality of actuators, thereby initiating a first nystagmus test of the plurality of nystagmus tests,
activate the image recorder in response to detecting operation of the function switch,
provide feedback associated with the first timer and at a plurality of predetermined times,
determine completion of the first timer,
store in memory the at least one of still images or video images captured by the image recorder, and
provide, in response to completion of the first timer and via a backlit actuator, a visual cue to the user indicating a next actuator of the plurality of actuators corresponding to a next nystagmus test to be selected from a predetermined order of the plurality of nystagmus tests.

2. The handheld device of claim 1, wherein the feedback is one selected from the group of tactile feedback, visual indications, or auditory indications, or each possible set or subset of tactile feedback, visual indications, and auditory indications.

3. The handheld device of claim 1, further comprising:
a haptic motor configured to provide tactile feedback associated with any one timer of the plurality of timers.

4. The handheld device of claim 1, further comprising:
a generally cylindrical-shaped housing including a first elongated surface, an opposed second elongated surface, a first end, and a second end.

5. The handheld device of claim 4, further comprising:
at least one light source disposed on the first elongated surface; and
an ultra-violet light source and a white-light source both disposed at or adjacent the first end.

6. The handheld device of claim 1, wherein the function switch is a first function switch, and wherein the processing circuitry is further configured to
initiate a second timer of the plurality of timers in response to detecting activation of a second actuator of the plurality of actuators,
activate the image recorder in response to detecting operation of a second function switch,
determine completion of the first timer, and
store in memory additional still images or video images captured by the image recorder.

7. The handheld device of claim 1, further comprising:
a communications port configured for electronic transfer of the still images or video images to an external device.

8. The handheld device of claim 1, wherein the first timer is associated with a first portion of the substance evaluation protocol and is an Equal Tracking timer.

9. The handheld device of claim 8, wherein the plurality of actuators further includes a second actuator selectable to activate a second timer, wherein the second timer is associated with a second portion of the substance evaluation protocol and is a Smooth Pursuit timer.

10. The handheld device of claim 9, wherein the plurality of actuators further includes a third actuator selectable to activate a third timer, wherein the third timer is associated with a third portion of the substance evaluation protocol and is a Maximum Deviation timer.

11. The handheld device of claim 10, wherein the plurality of actuators further includes a fourth actuator selectable to activate a fourth timer, wherein the fourth timer is associated with a fourth portion of the substance evaluation protocol and is an Angle of Onset timer.

12. The handheld device of claim 11, wherein the plurality of actuators further includes a fifth actuator selectable to activate a fifth timer, wherein the fifth timer is associated with a fifth portion of the substance evaluation protocol and is a Vertical Nystagmus timer.

13. A handheld testing device for facilitating a Drug Evaluation and Classification Examination, the device comprising:
a cylindrical housing having a longitudinal axis, the cylindrical housing including a first end and a second end opposite the first end along the longitudinal axis;
a camera positioned at a first surface of the cylindrical housing, the camera configured to capture at least one of still images or video images;
a plurality of timers, each of which is associated with one or more portions of a substance evaluation protocol, the substance evaluation protocol including the performance of a plurality of nystagmus tests; and
a plurality of actuators on a second surface of the cylindrical housing radially opposite the first surface, wherein the plurality of actuators are arranged linearly along the longitudinal axis, wherein each actuator is configured to provide tactile feedback when actuated, wherein a subset of the plurality of actuators includes backlit buttons configured to provide visual cues to a user indicating a next actuator of the plurality of actuators corresponding to a next nystagmus test to be selected from a predetermined order of the plurality of nystagmus tests, wherein one actuator of the plurality of actuators is configured to operate the camera, and wherein two or more of the plurality of actuators are configured to activate an associated one of the plurality of timers.

14. The device of claim 13, further comprising:
a first light source proximal the first end on a first surface of the cylindrical housing; and
a second light source positioned between the camera and the second end on the first surface.

15. The device of claim 14, wherein the camera is positioned on the cylindrical housing between the first light source and the second end on the first surface.

16. The device of claim 14, wherein the first light source includes a red light emitting diode, and wherein the second light source includes a white light emitting diode.

17. The device of claim 13, further comprising:
a haptic motor configured to provide tactile feedback associated with any one timer of the plurality of timers.

18. The device of claim 13, further comprising:
a communications port configured for electronic transfer of the still images or video images to an external device.

19. A handheld testing device comprising:
a housing configured to be held in one hand of a user administering an evaluation;
at least one light source disposed substantially within the housing and configured to be visible to a test subject facing the user, as the user moves the handheld test device in front of the eyes of the test subject;
a first backlit button selectable to activate an Equal Tracking timer, the equal tracking timer configured to control a first series of tactile feedback indications delineating sub-portions of an Equal Tracking nystagmus test;
a second backlit button different from the first backlit button, the second backlit button selectable to activate a Smooth Pursuit timer, the Smooth Pursuit timer configured to control a second series of the tactile feedback indications delineating sub-portions of a Smooth Pursuit nystagmus test;
at least a second light source, wherein the second light source comprises one or more of an ultraviolet light source, disposed substantially within the housing and configured for one or more investigatory purposes independent of or supplemental to a nystagmus test;
a third backlit button selectable to activate a Maximum Deviation timer corresponding to a Maximum Deviation nystagmus test;
a fourth backlit button selectable to activate an Angle of Onset timer corresponding to an Angle of Onset nystagmus test;
a fifth backlit button selectable to activate a Vertical Nystagmus timer corresponding to a Vertical Nystagmus test; and
wherein the backlit buttons are configured to provide visual cues to the user indicating a next backlit button corresponding to a next nystagmus test to be selected from a predetermined order of the Equal Tracking nystagmus test, the Smooth Pursuit nystagmus test, the Maximum Deviation nystagmus test, the Angle of Onset nystagmus test, and the Vertical Nystagmus test.

20. The handheld testing device of claim 19, further comprising:
a plurality of fixed-interval timers, the plurality of fixed-interval timers measuring respective fixed intervals and configured to provide at least a tactile feedback notification upon expiration of the respective fixed intervals, wherein the plurality of fixed-interval timers are configured to be activated in response to user selection of a combination of one or more buttons.

* * * * *